United States Patent [19]

Corbet et al.

[11] Patent Number: 4,617,377

[45] Date of Patent: Oct. 14, 1986

[54] SYNERGISTINE DERIVATIVES AND THEIR PREPARATION

[75] Inventors: Jean-Pierre Corbet, Ecully; Claude Cotrel, Paris; Daniel Farge, Thiais; Jean-Marc Paris, Vaires sur Marne, all of France

[73] Assignee: Rhone-Poulenc Sante, Courbevoie, France

[21] Appl. No.: 630,256

[22] Filed: Jul. 12, 1984

[30] Foreign Application Priority Data

Jul. 13, 1983 [FR] France .................................. 83 11706

[51] Int. Cl.$^4$ ............................................. C07K 5/12
[52] U.S. Cl. ................................................. 530/317
[58] Field of Search ................... 260/112.5 R

[56] References Cited
PUBLICATIONS

J. Preud'homme, P. Tarridec et A. Belloc, pp. 585–591 (1967).
Chem. Abstr., vol. 99, (1983) 212905.
Chem. Abstr., vol. 76, (1972) 127404.
Chem. Abstr., vol. 63, (1965) 13408.
Merck Index, 9th Edition, (1976), "Mikamycin" and Virginiamycin.
Mutton et al. Chemotherapy 29, 218 (1983).
Mattei et al., La Presse Medicale 29, 1789 (1984).
Rollmann et al., Pharm. Acta Helv. 50 (12) 455 (1975).

*Primary Examiner*—Delbert R. Phillips
*Attorney, Agent, or Firm*—Stevens, Davis, Miller & Mosher

[57] ABSTRACT

The invention provides new synergistine derivatives of the formula:

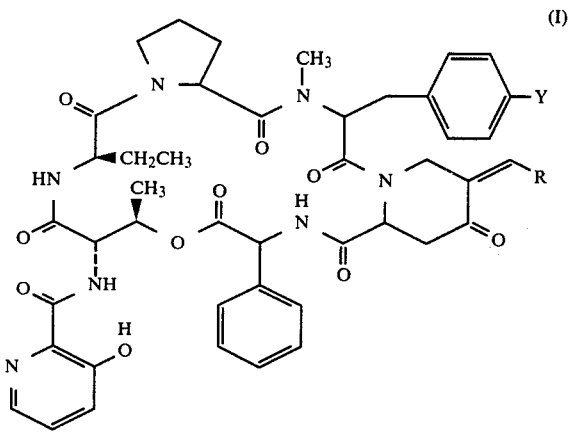

(I)

in which Y=H or N(CH$_3$)$_2$ and R represents:
(a) H or OH,
(b) a radical of the formula NR$_1$R$_2$, in which R$_1$ and R$_2$=H, phenyl or pyridyl (optionally substituted by dialkylamino (1 to 4 C), alkyl (1 to 10 C) [optionally substituted by OH, SH, COOH, anilino, or alkylamino or dialkylamino of which at least one of the alkyl parts is substituted by OH, SH, COOH or anilino 9 , alkenyl (3 or 4 C) or alkynyl (3 or 4 C), or alternatively R$_1$ and R$_2$ together form a heterocycle optionally containing another heteroatom such as O, S or N (optionally substituted by alkyl), or
(c) a halogen atom, a trimethylsilyloxy or dialkylphosphoryloxy radical or a radical —OSO$_2$R$_3$ or —O-COR$_4$, R$_3$ being alkyl, trifluoromethyl, trichloromethyl or optionally substituted phenyl and R$_4$ being defined in the same way as R$_3$ or being an acylalkyl, alkoxycarbonylalkyl or alkoxy radical, and also their salts and their preparation. These products are useful as intermediates in the synthesis of anti-bacterial synergistine derivatives.

7 Claims, No Drawings

SYNERGISTINE DERIVATIVES AND THEIR PREPARATION

Pristinamycin and virginiamycin are known synergistine derivatives: J. Preud'homme et al., Bull. Soc. Chim. Fr., 2, 585–91 (1968).

The present invention provides new synergistine derivatives of the formula:

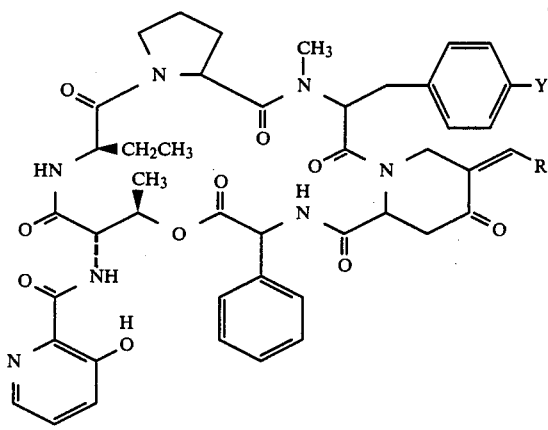

which are useful as intermediates for the preparation of other, therapeutically active synergistine derivatives, and their salts where they exit.

In formula (I), Y represents a hydrogen atom or a dimethylamino radical and R represents:
(a) a hydrogen atom or a hydroxyl radical,
(b) a radical of the formula:

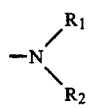

(II)

in which $R_1$ and $R_2$, which are identical or different, represent a hydrogen atom, a phenyl or pyridyl radical which is optionally substituted (by a dialkylamino radical in which each alkyl contains 1 to 4 carbon atoms in a linear or branched chain), an alkyl radical containing 1 to 10 carbon atoms in a linear or branched chain, which is optionally substituted [by a hydroxyl, mercapto, carboxyl, pyridyl or anilino radical or an alkylamino or dialkylamino radical in which at least one alkyl is itself substituted by a hydroxyl, mercapto, carboxyl or anilino radical], an alkenyl radical of 3 or 4 carbon atoms or an alkynyl radical of 3 or 4 carbon atoms, or alternatively $R_1$ and $R_2$ together form, with the nitrogen atom to which they are bonded, a 5-membered or 6-membered heterocyclic ring optionally containing another heteroatom such as oxygen, sulphur or nitrogen (optionally substituted by an alkyl radical), or
(c) a halogen atom, a trimethylsilyloxy or dialkylphosphoryloxy radical, or a radical of the formula:

or

in which $R_3$ is an alkyl, trifluoromethyl or trichloromethyl radical or a phenyl radical optionally substituted by a halogen atom or by an alkyl or nitro radical, and $R_4$ is defined in the same way as $R_3$ or represents an alkylcarbonylmethyl, 2-alkylcarbonylethyl, alkoxycarbonylmethyl, 2-alkoxycarbonylethyl or alkoxy radical.

It is understood that the alkyl radicals and portions which have been mentioned above or which are mentioned below are linear or branched (unless stated otherwise) and contain 1 to 4 carbon atoms each.

If the radical R represents a halogen atom, it can be chloride or bromine atoms.

The compounds of formula (I) in which R is other than a radical of the formula (II) can exist in 2 isomeric forms and these isomers and their mixtures fall within the scope of the present invention.

According to a feature of the invention, the compounds of the formula (I) are prepared by reacting a compound of the formula:

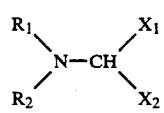

(III)

[in which $R_1$ and $R_2$ are alkyl radicals containing 1 to 4 carbon atoms each or together form, with the nitrogen atom to which they are bonded, a 5-membered or 6-membered heterocyclic ring as defined above under (b), and $X_1$ and $X_2$, which are identical or different, represent an alkoxy radical or a substituted amino radical defined in the same way as $-NR_1R_2$] with a compound of the formula:

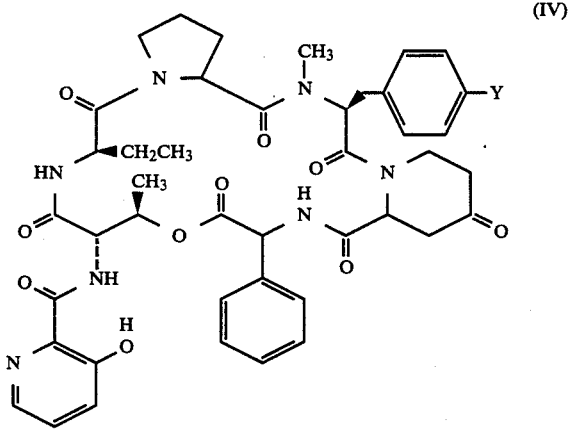

in which Y is defined as above, to give a compound of the formula (I) in which Y is as defined above and R represents a radical of the formula (II) in which $R_1$ and $R_2$ have the meanings given above for the formula (III), i.e. a compound of the formula:

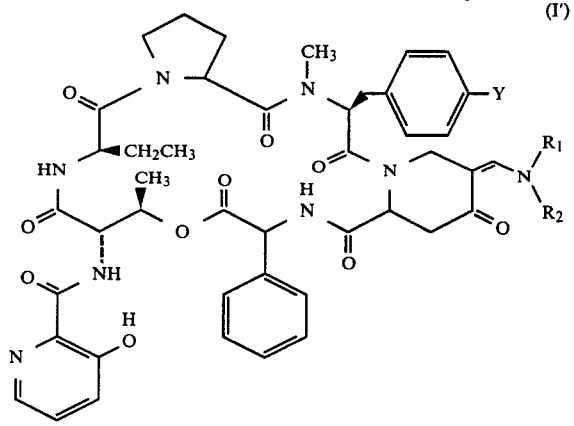

(I')

this reaction being followed, if appropriate, by:
(1)—reaction with an alkali metal borohydride, in the presence of a strong organic acid, to give a product of the formula (I) in which R represents a hydrogen atom,
(2)—a transenamination by reaction with an amine of the formula:

(V)

[in which R'$_1$ and R'$_2$ have the meanings given above for R$_1$ and R$_2$, except for the meanings defined for the formula (III)] to give a product of the formula (I) in which Y is as defined above and R represents a radical of the formula (II) in which R$_1$ and R$_2$ are defined in the same way as R'$_1$ and R'$_2$ above, or
(3)—hydrolysis to give a product of the formula:

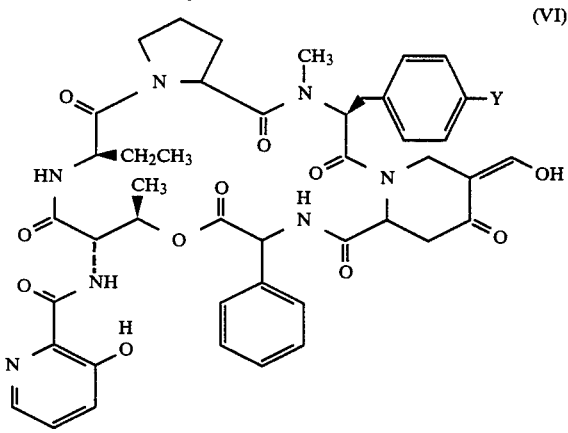

(VI)

and then, if appropriate, by conversion to a product of the formula (I) in which R is as defined above under (c), by reaction with a halogenating agent or a compound of the formula:

R'X    (VII)

in which R' is a trimethylsilyloxy or dialkylphosphoryloxy radical or a radical —OSO$_2$R$_3$ or —OCOR$_4$ and X represents a halogen atom.

If a product of the general formula (I') is prepared using a reactant of the formula (III) in which X$_1$ and/or X$_2$ represent a substituted amino radical, it is preferable to choose X$_1$ and/or X$_2$ so that the substituted amino radical is identical to the group —NR$_1$R$_2$ present on the molecule. t-Butoxybis(dimethylamino)methane is advantageously used.

In practice, the reaction of the compound of the formula (III) with the compound of the formula (IV) is generally carried out in an organic solvent such as a chlorinated solvent (e.g. 1,2-dichloroethane) or an amide (e.g. dimethylformamide), at a temperature of 0° to 25° C., preferably at a temperature of the order of 20° C.

The reaction of an alkali metal borohydride with the compound of the general formula (I') is generally carried out using sodium borohydride or cyanoborohydride in an organic solvent such as an ether (e.g. tetrahydrofuran) or an alcohol (e.g. isopropanol), in the presence of a strong organic acid such as trifluoroacetic acid, at a temperature of between 0° C. and the reflux temperature of the reaction mixture. The reaction is preferably carried out at a temperature of the order of 20° C.

The reaction of the amine of the formula (V) with the compound of the general formula (I') is generally carried out in an organic solvent such as acetic acid or an alcohol (e.g. ethanol), at a temperature of 0° C. to 25° C., preferably at a temperature of the order of 20° C.

The hydrolysis of the compound of the formula (I') to give the compound of the formula (VI) is generally carried out in a dilute acid at a temperature of the order of 20° C. A 0.1N solution of hydrochloric acid is advantageously used.

If a product of the formula (I) in which R is a halogen atom is prepared by reacting a halogenating agent with a synergistine derivative of the formula (VI), it is advantageous to use a halogen derivative of phosphorus, in particular halogen/triarylphosphite addition compounds, or alternatively
dichlorotriphenylphosphorane or catechyltrichlorophosphorane if R is a chlorine atom, or
catechyltribromophosphorane if R is a bromine atom.
The reaction is generally carried out in a chlorinated solvent such as methylene chloride, at a temperature of between −20° and +20° C.

If a compound of the formula (VII) is reacted with a synergistine derivative of the formula (VI), it is preferred to use a product in which X is a chlorine or bromine atom.

The reaction is generally carried out in an organic solvent such as methylene chloride, in the presence of an acid acceptor such as an organic base like triethylamine or an inorganic base like an alkali metal carbonate or bicarbonate, e.g. sodium bicarbonate or potassium bicarbonate. The reaction temperature is generally from −20° to +20° C.

The compounds of the formula (III) can be prepared by the methods described by H. Bredereck et al., Chem. Ber. 101, 41 (1968), Chem. Ber. 101, 3958 (1968) and Chem. Ber. 106, 3725 (1973).

The compounds of the formula (IV) are the known synergistine derivatives pristinamycin I$_A$ when Y represents dimethylamino and virginiamycin S when Y represents hydrogen.

The compounds of the formula (I) are useful in particular as intermediates for the preparation of therapeutically active synergistine derivatives of the formula:

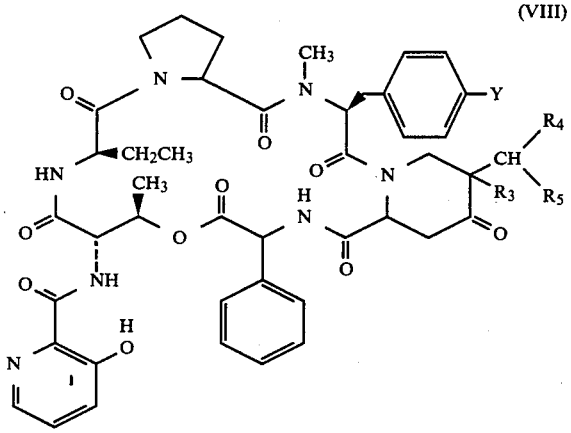

(VIII)

in which Y represents a hydrogen atom or a dimethylamino radical and (A) either $R_5$ and $R_6$ each represent a hydrogen atom and $R_4$ represents a pyrrolidin-3-ylthio radical or a piperidin-3-ylthio or piperidin-4-ylthio radial (these radicals being optionally substituted by an alkyl radical) or alternatively $R_4$ represents an alkylthio radical substituted by one or two hydroxysulphonyl, alkylamino or dialkylamino radicals or by one or two rings chosen from piperazino (optionally substituted by an alkyl radical), morpholino, thiomorpholino, piperidino, pyrrolidin-1-yl, piperidin-2-yl, piperidin-3-yl or piperidin-4-yl and pyrrolidin-2-yl or pyrrolidin-3-yl (these last five rings being optionally substituted on the nitrogen atom by an alkyl radical), (B) or $R_5$ and $R_6$ together form a valance bond and $R_4$ represents a pyrrolidin-3-ylamino, piperidin-3-ylamino or piperidin-4-ylamino, pyrrolidin-3-yloxy, piperidin-3-yloxy or piperidin-4-yloxy, pyrrolidin-3-ylthio, piperidin-3-ylthio or piperidin-4-ylthio radical (these radicals being optionally substituted on the nitrogen atom of the ring by an alkyl radical) or alternatively $R_4$ represents an alkylamino, alkoxy or alkylthio radical substituted by one or two hydroxysulphonyl, alkylamino, dialkylamino, trialkylammonio or imidazol-4-yl or imidazol-5-yl radicals or by one or two rings chosen from piperazino (optionally substituted by an alkyl radical), morpholino, thiomopholino, piperidino, pyrrolidin-1-yl, piperidin-2-yl, piperidin-3-yl or piperidin-4-yl and pyrrolidin-2-yl or pyrrolidin-3-yl (these last two rings being optionally substituted on the nitrogen atom by an alkyl radical), it being understood that, in the general formula (VIII), the alkyl radicals and alkyl portions contain 1 to 5 carbon atoms and are in a linear or branched chain.

To obtain the therapeutically active compounds of the formula (VIII), the compounds of formula (I) according to the invention can be used in the following way:

1. To prepare a compound of the formula (VIII) in which the symbols are as defined above under (A), a compound of the formula:

$$R'_4-H \qquad (IX)$$

in which $R'_4$ has the definition given above under (A) for $R_4$ is reacted with a compound of the formula (I) in which Y is defined as above and R represents a hydrogen atom.

The reaction is generally carried out in an organic solvent such as an alcohol like methanol or a chlorinated solvent like chloroform, or a mixture of these solvents, at a temperature of between 0° C. and the reflux temperature of the reaction mixture, preferably at a temperature of 20° C.

2. To prepare a compound of the formula (VIII) in which the symbols are defined as above under (B), except that $R_4$ cannot represent a pyrrolidin-3-yloxy, piperidin-3-yloxy or piperidin-4-yloxy or alkoxy radical [optionally substituted as defined under B)], a compound of the formula:

$$R''_4-H \qquad (X)$$

in which $R''_4$ has the definition given above under (B) for $R_4$, except that it cannot represent a pyrrolidin-3-yloxy, piperidin-3-yloxy or piperidin-4-yloxy or alkoxy radical [optionally substituted as defined under B)], is reacted with a compound of the formula (I) in which R is defined as above under (b).

The reaction is generally carried out in an acid medium (e.g. acetic acid), with or without a solvent, at a temperature of between 0° and 50° C., preferably at a temperature of the order of 20° C., if appropriate in the presence of catalytic quantities of trifluoroacetic acid. The solvent used may be an ether (e.g. tetrahydrofuran), alcohol (e.g. ethanol) or chlorinated solvent (e.g. methylene chloride or chloroform).

3. To prepare a compound of the formula (VIII) in which the symbols are defined as above under (B), a compound of the formula:

$$R'''_4-H \qquad (XI)$$

in which $R'''_4$ has the definition given above under (B) for $R_4$, is reacted with a compound of the formula (I) in which R is defined as above under (c).

The reaction is generally carried out in an organic solvent such as an ether (e.g. tetrahydrofuran), an alcohol (e.g. ethanol) or a chlorinated solvent (e.g. methylene chloride or chloroform), at a temperature of the order of 20° C., in the presence of a base such as an alkali metal hydride or an alkali metal alcoholate, e.g. sodium ethylate or potassium t-butylate. If $R'''_4$ is other than a substituted alkoxy radical or a heterocyclyloxy radical, the reaction can also be carried out either in a neutral medium, at a temperature of 0° C. to 50° C., in one of the abovementioned solvents, or in an acid medium under identical conditions to those described above for reacting a compound of the formula (XVI) with a compound of the formula (XIV).

To prepare the therapeutically active compounds of the formula (VIII), it will be understood that, if the various radicals in the general formula (IX, (X) or (XI) contain a secondary amine group capable of interfering with the reaction, this must be protected by means of a protecting radical before the compounds of the formula (I) are reacted, and the protecting radical must then be removed after the reaction. Any blocking means normally employed for protecting a secondary amine group and able to be removed thereafter, without affecting the rest of the molecule, may be used for this purpose. It is particularly advantageous to use the trifluoroacetyl radical as the protecting radical. This can then be removed using an aqueous solution of an alkali metal bicarbonate such as sodium bicarbonate or potassium bicarbonate.

The synergistines obtained by fermentation are used for the treatment of infections caused by Grampositive bacteria (of the genus Staphylococcus, Streptococcus, Pneumococcus or Enterococcus) and Gramnegative bacteria (of the genus Haemophilus, Gonococcus or Meningococcus). However, known synergistines have the disadvantage of being insoluble in an aqueous medium and they can therefore only be administered orally, generally in the form of capsules, coated tablets or ordinary tablets. In view of this insolubility, it is impossible to use the synergistines known hitherto if the patient is not capable of swallowing; this is the case, in particular, in paediatrics and intensive care, whereas the spectrum of activity of these products would make them a valuable indication in a large number of circumstances, e.g. in cases of comatose septicaemia.

The products of the formula (VIII) have the considerable advantage of being able to be solubilized in water, in the form of salts, at therapeutically usable doses while at the same time retaining the general spectrum of activity of synergistines.

They are especially active in vitro against *Staphylococcus aureus* Smith at concentrations of between 0.1 and 125 μg/ml.

Their toxicity is generally low. Their $LD_{50}$ is generally greater than 300 mg/kg, administered subcutaneously to mice.

The compounds of the formula (I) and also the therapeutically active products of the formula (VIII) can be purified by the usual methods such as crystallization, chromatography and, if necessary, successive extractions in an acidic or basic medium. For those skilled in the art who are familiar with the sensitivity of synergistines in an alkaline medium, it is obvious that the term "basic medium" is understood as meaning a medium which is just sufficiently alkaline to free the parent substance from its acid addition salt, i.e. a medium whose pH does not exceed 7.5 to 8.

When the new compounds of formula (I) exist in isomeric forms, these can be separated, e.g. by high performance liquid chromatography.

The compounds of formula (I) can also be converted, if necessary, into addition salts with acids by reaction with an acid in an organic solvent such as an alcohol, a ketone, an ester or a chlorinated solvent. The salt precipitates, if appropriated after concentration of its solution; it is separated by filtration or decantation. The acid addition salts can also be obtained in the form of aqueous solutions by the addition of an aqueous solution of the corresponding acid to the compound of formula (I).

The compounds of formula (I) in which R represents a radical containing a carboxyl group can be converted into metal salts or into addition salts with nitrogen bases in a manner analogous to that described above for the acid addition salts, except that the acid is replaced with a metal hydroxide or a nitrogen base.

Examples of salts which may be mentioned are the addition salts with mineral acids, such as hydrochlorides, hydrobromides, hydroiodides, sulphates, nitrates and phosphates, or with organic acids, such as acetates, propionates, succinates, maleates, fumarates, methanesulphonates, p-toluenesulphonates, isethionates, trifluoroacetates and oxalates, or substitution derivatives of these compounds, and the salts with alkali metals or alkaline earth metals, such as potassium, sodium, lithium and magnesium, and also the addition salts with organic nitrogen bases such as dimethylamine, diethylamine, diisopropylamine, dicyclohexylamine, N-ethylpiperidine, N-methylmorpholine and ethanolamine.

Of particular value are the compounds of formula (I) in which Y is as defined above and R represents a hydrogen atom, a hydroxyl radical, or a radical —$NR_1R_2$ in which $R_1$ and $R_2$ each represent a hydrogen atom, a phenyl radical optionally substituted by a dialkylamino radial, an alkyl radical which is optionally substituted [by a hydroxyl, mercapto, carboxyl, pyridyl or anilino radical or an alkylamino or dialkylamino radical in which the alkyl is substituted by hydroxyl or an alkynyl radical of 3 or 4 carbon atoms.

Among these products, the following are of more particular value:

5δ-dimethylaminomethylenepristinamycin $I_A$
5δ-dimethylaminomethylenevirginiamycin S
5δ-hydroxymethylenepristinamycin $I_A$
5δ-methylenevirginiamycin S.

The following products are also of value:
5-trifluoroacetoxymethylenepristinamycin $I_A$
5-trifluoroacetoxymethylenevirginiamycin S.

The Examples which follow illustrate the invention. The application Examples show how the products of the invention can be converted into therapeutically active compounds of the formula (VIII). The NMR spectra of the products described in the Examples and application Examples have general characteristics which are common to all the products and particular characteristics which are peculiar to each of the products according to the variable substituents in the general formulae (I) and (VIII). In Example 1, the assignment of all the protons in the molecule is given; in the subsequent Examples and application Examples, only the particular characteristics due to the variable radicals are mentioned. All the protons are designated according to the numbering indicated in the following basic formula and recommended by J. O. ANTEUNIS et al [Eur. J. Biochem., 58, 259 (1975)].

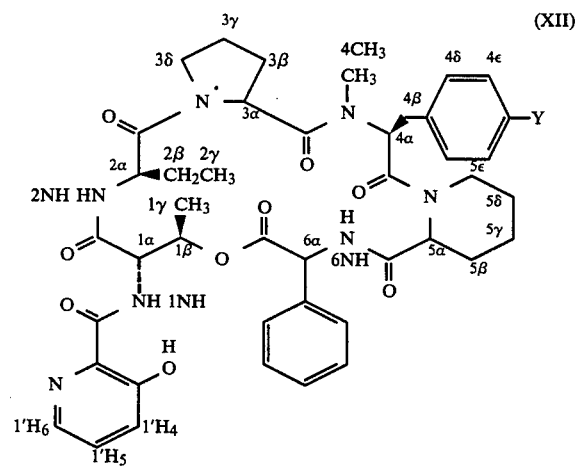

All the spectra were run at 250 MHz in deuterochloroform; the chemical shifts are expressed in ppm relative to the signal for tetramethylsilane. The abbreviations used below are as follows:

s=singlet
d=doublet
t=triplet
mt=multiplet up=unresolved peaks
dd=doublet of doublets
dt=doublet of triplets
ddd=doublet of doublet of doublets
dddd=doublet of doublet of doublet of doublets In Examples 2 to 24 and also in the application examples, the following are given respectively in brackets: the chemical shift, the shape of the signal, the integration (number of protons, if appropriate with the percentage of isomers) and the assignment of the protons.

In the examples and application examples which follow, "flash" chromatography is understood as meaning a purification technique which comprises using a short chromatography column and operating under a moderate pressure (50 kPa) using a silica of particle size 40–63 μm, according to W. C. STILL, M. KAHN and A. MITRA [J. Org. Chem., 43, 2923 (1978)].

EXAMPLE 1

Tert.-butoxybis(dimethylamino)methane (230 cc) is added to a solution of pristinamycin $I_A$ (46 g) in 1,2-dichloroethane (460 cc); the solution obtained is stirred for 18 hours at a temperature of the order of 20° C. The reaction mixture is diluted with methylene chloride (1 liter) and then washed 3 times with a 0.4% aqueous solution of ammonium chloride (3 liters in total). The organic phase is dried over magnesium sulphate and filtered and the filtrate is then concentrated to dryness under reduced pressure (2.7 kPa) at 30° C. The residue obtained is triturated with distilled water (600 cc); the mixture is filtered and the filtrate is dried and concentrated to dryness under reduced pressure (2.7 kPa) at 20° C. This gives crude 5δ-dimethylaminomethylenepristinamycin $I_A$ (41 g) in the form of a beige powder. This product is of sufficient quality to be used as such in the subsequent syntheses. However, it can be purified in the following manner:

Crude 5δ-dimethylaminomethylenepristinamycin $I_A$ (23.5 g) is chromatographed by "flash" chromatography, eluent: chloroform/methanol [98/2 by volume]. Fractions 16 to 25 are combined and concentrated to dryness under reduced pressure (2.7 kPa) at 30° C.

This gives 5δ-dimethylaminomethylenepristinamycin $I_A$ (12 g) in the form of a white powder melting at about 195° C.

| δ (ppm) | Shape | Assignment |
| --- | --- | --- |
| 11.6 | s | OH |
| 8.65 | d | 6NH |
| 8.40 | d | 1NH |
| 7.75 | dd | $1'H_6$ |
| 7.40 | s | =CH—N$\diagdown^\diagup$ |
| 7.35 to 7.20 | up | $6\gamma + 6\delta + 6\epsilon + 1'H_4 + 1'H_5$ |
| 6.95 | dd ⎫ AB system | $4\epsilon + 4\delta$ |
| 6.55 | d ⎭ | |
| 6.55 | up | 2NH |
| 5.85 | up | 1β |
| 5.77 | d | 6α |
| 5.50 | d | $5\epsilon_1$ |
| 5.25 | dd | 4α |
| 5.17 | d | 5α |
| 4.85 | dd | 1α |
| 4.80 | up | 2α |
| 4.55 | dd | 3α |
| 3.70 | d | $5\epsilon_2$ |
| 3.50 and 3.30 | up | $3\delta_1 + 3\delta_2$ |
| 3.2 | s | $4NCH_3$ |
| 3.10 | s | =CH—N($CH_3$)$_2$ |
| 2.94 | s | $4N(CH_3)_2$ |
| 2.94 | up | 4β |
| 2.50 | d | $5\beta_1$ |
| 2.05 | up | $3\beta_1$ |
| 1.60 | up | $2\beta_1 + 2\beta_2 + 3\gamma_1$ |
| 1.25 | d | 1γ |
| 1.22 | up | $3\beta_2 + 3\gamma_2$ |
| 1 | dd | $5\beta_2$ |
| 0.9 | t | 2γ |

EXAMPLE 2

By following a procedure analogous to that described in Example 1, but starting from virginiamycin S (2 g) and bis(dimethylamino)tert.-butoxymethane (10 cc), and after purification by flash chromatography [eluent: chloroform/methanol (98/2 by volume)] and concentration to dryness of fractions 9 to 12 under reduced pressure (2.7 kPa) at 30° C., 5δ-dimethylaminomethylenevirginiamycin S (0.8 g) is obtained in the form of a yellow powder melting at about 175° C.

NMR spectrum: 0.9 (up; 4H: $2\gamma+5\beta_2$), 3.05 (s; 6H: =CH—N($CH_3$)$_2$), 3.65 (d; 1H: $5\epsilon_2$), 4.85 (d; 1H: $5\epsilon_1$), 5.15 (dd; 1H: 5α), 7.10 to 7.40 (up; aromatic protons+=C$\underline{H}$N<), 7.70 (dd; 1H: $1'H_6$).

EXAMPLE 3

A 4N ethanolic solution of gaseous ammonia (10 cc) is added slowly to a solution of 5δ-dimethylaminomethylenepristinamycin $I_A$ (1.84 g) in acetic acid (20 cc). The solution obtained is stirred for 20 hours at a temperature of the order of 20° C. and is then poured slowly into a saturated aqueous solution of sodium bicarbonate (200 cc). The suspension obtained is extracted 3 times with methylene chloride (300 cc in total); the organic phases are combined, dried over magnesium sulphate and filtered and the filtrate is concentrated to dryness under reduced pressure (2.7 kPa) at 30° C. The residue obtained is purified by "flash" chromatography [eluent: chloroform/methanol (92/8 by volume)]. By concentration to dryness of fractions 11 to 13 under reduced pressure (2.7 kPa) at 30° C., 5δ-aminomethylenepristinamycin $I_A$ (1.3 g) is obtained in the form of a beige powder melting at about 190° C.

NMR spectrum: 0.7 to 1.10 (mt, 4H: $2\gamma+5\beta_2$), 7.15 to 7.53 (mt, 9H (including 1 exchangeable): $6\gamma+6\delta+6\epsilon+1H$ of the $NH_2+=C\underline{H}—NH_2+1'H_4+1'H_5$), 9.12 (s broad, 1H (exchangeable); 1H of the $NH_2$).

EXAMPLE 4

By following a procedure analogous to that described in Example 3, but starting from 5δ-dimethylaminomethylenepristinamycin $I_A$ (1.84 g) and a 7N ethanolic solution of methylamine (1.9 cc), and after purification by "flash" chromatography [eluent: chloroform/methanol (98/2 by volume)] and concentration to dryness of fractions 16 and 17 under reduced pressure (2.7 kPa) at 30° C., 5δ-methylaminomethylenepristinamycin $I_A$ (0.9 g) is obtained in the form of a yellow powder melting at about 180° C.

NMR spectrum: 0.98 (dd, 1H; $5\beta_2$), 3.01 (d, 3H: —NHC$\underline{H}_3$), 7.17 to 7.42 (up, 8H:

6γ+6δ+6ε+1'H₅+1'H₄+=CHNHCH₃), 9.80 (mt, 1H (exchangeable): NHCH₃).

EXAMPLE 5

By following a procedure analogous to that described in Example 3, but starting from 5δ-dimethylaminomethylenepristinamycin I$_A$ (1.84 g) and decylamine (3.1 g), and after purification by "flash" chromatography [eluent: chloroform/methanol (98/2 by volume)] and concentration to dryness of fractions 6 and 7 under reduced pressure (2.7 kPa) at 30° C., 5δ-decylaminomethylenepristinamycin I$_A$ (1.3 g) is obtained in the form of a beige powder melting at about 120° C.

NMR spectrum: 0.8 to 1.0 (mt; 7H: 2γ+5β₂+—(CH₂)₉CH₃), 1.10 to 1.45 (up; 21H: 1γ+3β₂+—CH₂(CH₂)₈CH₃), 3.10 to 3.45 (up; 7H: 4NCH₃+3δ₂+4β₁+=CH—CH₂(CH₂)₈—), 7.20 to 7.50 (up; 8H: 6γ+6δ+6ε+1'H₅+1'H₄+—CH—NH—), 9.95 (up; 1H (exchangeable): =CH—NH—).

EXAMPLE 6

By following a procedure analogous to that described in Example 3, but starting from 5δ-dimethylaminomethylenepristinamycin I$_A$ (1.84 g) and pyrrolidine (1.42 g), and after purification by "flash" chromatography [eluent: chloroform/methanol (98/2 by volume)] and concentration to dryness of fractions 12 to 22 under reduced pressure (2.7 kPa) at 30° C., 5δ-(pyrrolidin-1-ylmethylene)pristinamycin I$_A$ (0.8 g) is obtained in the form of a yellow powder melting at about 260° C.

NMR spectrum: 0.9 (mt; 4H: 2γ+5β₂), 1.48 to 2.08 (up; 8H: 2β₇+2β₂+3γ₁+3β₁+

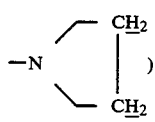

3.4 to 3.79 (up; 6H: 3δ₁+5ε₂+

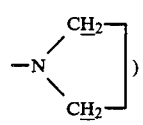

7.67 (s; 1H: =CH—N<).

EXAMPLE 7

By following a procedure analogous to that described in Example 3, but starting from 5δ-dimethylaminomethylenepristinamycin I$_A$ (1.84 g) and N-methylpropargylamine (1.4 g), and after purification by "flash" chromatography [eluent: ethyl acetate/methanol (90/10 by volume)] and concentration to dryness of fractions 9 to 21 under reduced pressure (2.7 kPa) at 30° C., 5δ-(N-methylpropargylamino)methylenepristinamycin I$_A$ (0.7 g) is obtained in the form of a yellow powder melting at about 175° C.

NMR spectrum: 0.72 (dd; 1H: 5β₂), 2.32 to 2.58 (mt+t; 2H: 5β₁+—C≡C—H), 3.05 to 3.37 (up; 8H: —NCH₃+4—NCH₃+3γ₂+4β₁), 4 (mt; 2H:

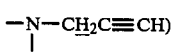

7.06 to 7.54 (up; 8H: 6γ+6δ+6ε, =CH—N<+1'H₄+1'H₅).

EXAMPLE 8

By following a procedure analogous to that described in Example 3, but starting from 5δ-dimethylaminomethylenepristinamycin I$_A$ (1.84 g) and aniline (0.36 g), and after purification by "flash" chromatography [eluent: ethyl acetate] and concentration to dryness of fractions 4 to 10 under reduced pressure (2.7 kPa) at 30° C., 5δ-phenylaminomethylenepristinamycin I$_A$ (1.6 g) is obtained, which melts at about 270° C. (with decomposition).

NMR spectrum: 0.95 (dd; 1H: 5β₂), 2.45 (d; 1H: 5β₁), 3.60 (d; 1H: 5ε₂), 5.05 (d; 1H: 5ε₁), 5.20 (d; 1H: 5α), 7.25 (d; 1H: —NH—C₆H₅), 7 to 7.50 (up; 13H: 6γ+6δ+6ε+1'H₄+1'H₅+—NH—C₆H₅+=CH—NH—), 7.75 (dd; 1H: 1'H₆).

EXAMPLE 9

By following a procedure analogous to that described in Example 3, but starting from 5δ-dimethylaminomethylenepristinamycin I$_A$ (0.90 g) and N-methylaniline (0.22 g), and after purification by "flash" chromatography [eluent: ethyl acetate/methanol (90/10 by volume)] and concentration to dryness of fractions 10 to 14 under reduced pressure (2.7 kPa) at 30° C., 5δ-(N-methylphenylamino)methylenepristinamycin I$_A$ (0.4 g) is obtained in the form of a yellow powder melting at about 170° C.

NMR spectrum: 0.90 (up; 4H: 5β₂+2γ), 2.50 (d; 1H: 5β₁), 3.50 (s; 3H:

5.15 (up; 2H: 4α+5α) 7.10 to 7.40 (up; 13H: 6γ+6δ+6ε+1'H₄+1'H₅+,

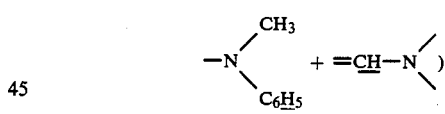

7.75 (dd; 1H: 1'H₆).

EXAMPLE 10

By following a procedure analogous to that described in Example 3, but starting from 5δ-dimethylaminomethylenepristinamycin I$_A$ (1.84 g) and 4-dimethylaminoaniline (1.36 g), and after purification by "flash" chromatography [eluent: chloroform/methanol (98/2 by volume)] and concentration to dryness of fractions 3 to 5 under reduced pressure (2.7 kPa) at 30° C., 5δ-(4-dimethylaminophenyl)aminomethylenepristinamycin I$_A$ (1 g) is obtained in the form of a brown powder melting at about 165° C.

NMR spectrum: 0.90 (up; 4H: 2γ+5β₂), 2.40 (d; 1H: 5β₁), 2.95 (s;

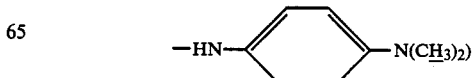

4.55 (d; 1H: 5ε₂), 5.05 (d; 1H: 5ε₁), 5.15 (up; 2H: 4α+5α), 7 (up; 4H:

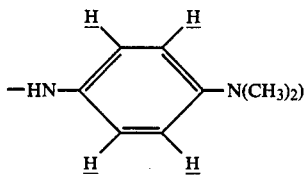

7.30 (in unresolved peaks: =C$\underline{H}$—NH—), 7.80 (dd; 1H: 1'H₆).

EXAMPLE 11

By following a procedure analogous to that described in Example 3, but starting from 5δ-dimethylaminomethylenepristinamycin I$_A$ (2.77 g) and N-(2-hydroxyethyl)propylenediamine (3.54 g), and after purification by "flash" chromatography [eluent: chloroform/methanol (85/15 by volume)] and concentration to dryness of fractions 19 to 25 under reduced pressure (2.7 kPa) at 30° C., 5δ-[3-(2-hydroxyethylamino)propyl]aminomethylenepristinamycin I$_A$ (0.95 g) is obtained in the form of a yellow powder melting at about 162° C.

NMR spectrum: 0.90 (1H under 2γ: 5β₂), 2.45 (d; 1H: 5β₁), 2.80 (up; 2H: =CH—NH—CH₂—), 3.15 (up; 4H: —CH₂—NH—CH₂—), 3.50 (broad d; 1H: 5ε₁), 3.75 (broad up; 1H: —CH₂—OH), 5.15 (broad s; 1H: 5α), 6.60 (up; 1H: —CH₂—N$\underline{H}$—CH₂—), 7.20 to 7.50 (up aromatic protons+=CH$\underline{N}$H—), 7.80 (dd; 1H: 1'H₆), 10.00 (broad up; 1H: =C$\underline{H}$—NH—).

EXAMPLE 12

By following a procedure analogous to that described in Example 3, but starting from 5δ-dimethylaminomethylenepristinamycin I$_A$ (2.76 g) and N-(3-aminopropyl)diethanolamine (4.86 g), and after purification by "flash" chromatography [eluent: chloroform/methanol (85/15 by volume)] and concentration to dryness of fractions 13 to 19 under reduced pressure (2.7 kPa) at 30° C., 5δ-[3-N-bis(2-hydroxyethyl)aminopropyl]aminomethylenepristinamycin I$_A$ (0.95 g) is obtained in the form of a yellow powder melting at about 164° C.

NMR spectrum: 0.90 (under the triplet of 2γ, 1H: 5β₂), 2.50 (d; 1H: 5β₁), 2.60 (up; 4H: 2 times

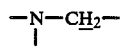

of the chain), 3.10 (up; 4H: 2 times

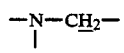

of the chain), 3.45 (broad d; 1H: 5ε₂), 3.65 (broad up; 4H: 2 times —CH₂OH), 4.90 (broad d; 1H: 5ε₁), 5.15 (broad d; 1H: 5α), 7.75 (dd; 1H: 1'H₆), 10.25 (up; 1H: =CH—N$\underline{H}$—).

EXAMPLE 13

By following a procedure analogous to that described in Example 3, but starting from 5δ-dimethylaminomethylenepristinamycin I$_A$ (1.84 g) and 2-aminoethanethiol (1.54 g), and after purification by "flash" chromatography [eluent: ethyl acetate/methanol (90/10 by volume)] and concentration to dryness of fractions 8 to 14 under reduced pressure (2.7 kPa) at 30° C., 5δ-(2-mercaptoethylamino)methylenepristinamycin I$_A$ (0.6 g) is obtained in the form of a yellow powder melting at about 160° C.

NMR spectrum: 0.90 (up; 4H: 2γ+5β₂), 1.45 (t; 1H: —S$\underline{H}$), 2.45 (d; 1H: 5β₁), 2.70 (up; 2H: —CH₂S—), 3.40 (up; 2H: —NH—CH₂—), 3.50 (d; 1H: 5ε₂), 4.95 (dd; 1H: 5ε₁), 7.15 to 7.50 (up; 8H: 6γ+6δ+6ε+1'H₄+1'H₅+=C$\underline{H}$—NH—), 7.80 (dd; 1H: 1'H₆), 10 (up; 1H: =CH—N$\underline{H}$—).

EXAMPLE 14

By following a procedure analogous to that described in Example 3, but starting from 5δ-dimethylaminomethylenepristinamycin I$_A$ (2.76 g) and N-phenylethylenediamine (4.08 g), and after purification by "flash" chromatography [eluent: chloroform/methanol (98/2 by volume)] and concentration to dryness of fractions 14 to 24 under reduced pressure (2.7 kPa) at 30° C., 5δ-(2-phenylaminoethyl)aminomethylenepristinamycin I$_A$ (1.2 g) is obtained in the form of a yellow powder melting at about 172° C.

NMR spectrum: 0.95 (under the methyl 2γ, 1H: 5β₂), 2.45 (d; 1H: 5β₁), 3.10-3.40 (up; 4H: —CH₂—CH₂NHC₆H₅), 3.45 (d; 1H: 5ε₂), 5.15 (broad d; 1$\overline{\text{H}}$: 5α), 6.55 to 6.80 (up; 4H:

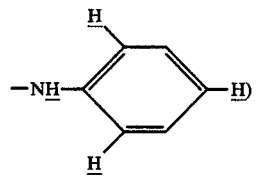

7.25 to 7.50 (up; without the aromatic protons: =CH—), 7.80 (dd; 1H: 1'H₆), 10.00 (up; 1H: =C$\underline{H}$—NH—).

EXAMPLE 15

By following a procedure analogous to that described in Example 3, but starting from 5δ-dimethylaminomethylenepristinamycin I$_A$ (1.84 g) and 2-(2-aminoethyl)-pyridine (2.44 g), and after purification by "flash" chromatography [eluent: chloroform/methanol (95/5 by volume)] and concentration to dryness of fractions 9 to 12 under reduced pressure (2.7 kPa) at 30° C., 5δ-[2-(pyridin-2-yl)ethyl]aminomethylenepristinamycin I$_A$ (1.2 g) is obtained in the form of a yellow powder melting at about 170° C.

NMR spectrum: 0.90 (under t of 2γ, 1H: 5β₂), 2.45 (d; 1H: 5β₁), 3.25 (up; 2H: —CH₂—NH—), 3.45 (up; 3H: including 5ε₂), 4.85 (up; 3H: including 5ε₁), 5.10 (d; 1H: 5α), 7.10 to 7.45 (up; aromatic protons including 3H:

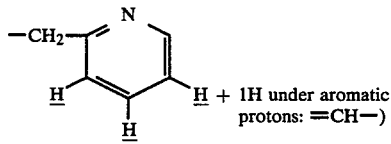

7.75 (dd; 1H: 1'H₆), 8.55 (broad d; 1H:

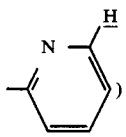

10.00 (up; 1H: NH—CH₂—).

EXAMPLE 16

By following a procedure analogous to that described in Example 3, but starting from 5δ-dimethylaminomethylenepristinamycin I$_A$ (1.84 g) and glycine (1.5 g), and after purification by "flash" chromatography [eluent: methylene chloride/methanol (80/20 by volume)] and concentration to dryness of fractions 9 to 16 under reduced pressure (2.7 kPa) at 30° C., 5δ-carboxymethylaminomethylenepristinamycin I$_A$ (0.7 g) is obtained in the form of an ochre powder melting at a temperature above 270° C.

The infra-red spectrum has the following bands characteristic of pristinamycins: 3300 cm⁻¹, 1745 cm⁻¹, 1660–1620 cm⁻¹, 1525 cm⁻¹, 810 cm⁻¹, 700 cm⁻¹ and also those of the group —CO₂⁻ (in the form of an internal salt): 1660 to 1620 cm⁻¹ and 1410 cm⁻¹.

EXAMPLE 17

Sodium cyanoborohydride (0.43 g) is added to a solution of 5δ-dimethylaminomethylenepristinamycin I$_A$ (12 g) in tetrahydrofuran (230 cc) containing trifluoroacetic acid (1.2 cc); the solution obtained is stirred for 4 hours at a temperature of the order of 20° C. and is then concentrated to dryness under reduced pressure (2.7 kPa) at 30° C. The residue obtained is purified by "flash" chromatography [eluent: chloroform/methanol (95/5 by volume)]; fractions 4 to 15 are concentrated to dryness under reduced pressure (2.7 kPa) at 30° C. This gives 5δ-methylenepristinamycin I$_A$ (5.5 g) in the form of white crystals melting at 245° C.

NMR spectrum: 0.55 (dd; 1H: 5β₂), 2.40 (d; 1H: 5β₁), 3.55 (dd; 1H: 5ε₂), 5.25 (up; 2H: 5α+5ε₁), 5.30 and 6.10 (2s; 2H:

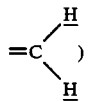

7.85 (dd; 1H: 1'H₆).

The 5δ-dimethylaminomethylenepristinamycin I$_A$ can be prepared as described in Example 1.

EXAMPLE 18

Trifluoroacetic acid (about 20 cc) is added over a period of 15 minutes to a solution of 5δ-dimethylaminomethylenepristinamycin I$_A$ (19.5 g) in isopropanol (570 cc), cooled to 5° C. Sodium borohydride (0.4 g) is subsequently added and the mixture is then stirred for 20 hours at a temperature of the order of 20° C. The reaction mixture is then concentrated to dryness under reduced pressure (2.7 kPa) at 30° C.; the residue obtained is dissolved in methylene chloride (400 cc). The solution is washed with distilled water (2×200 cc), dried over sodium sulphate and filtered and the filtrate is concentrated to dryness under reduced pressure (2.7 kPa) at 30° C. The residue is purified by "flash" chromatography [eluent: methylene chloride/methanol (97/3 by volume)]; by concentration to dryness of fractions 17 to 34 under reduced pressure (2.7 kPa) at 30° C., 5δ-methylenepristinamycin I$_A$ (5.7 g) is obtained in the form of a yellow powder melting at about 230° C. (crude product of sufficient purity to be used as such in the subsequent steps).

EXAMPLE 19

The procedure followed is analogous to that described in Example 17 for 5δ-methylenepristinamycin I$_A$, but 5δ-dimethylaminomethylenevirginiamycin S (2 g) and sodium cyanoborohydride (74 mg) are used as the starting materials. After purification by "flash" chromatography [eluent: chloroform/methanol (98/2 by volume)] and concentration to dryness of fractions 2 to 5 under reduced pressure (2.7 kPa) at 30° C., 5δ-methylenevirginiamycin S (1 g) is obtained in the form of a beige powder melting at about 190° C.

NMR spectrum: 0.35 (dd; 1H: 5β₂), 2.45 (dd; 1H: 5β₁), 3.55 (dd; 1H: 5ε₂), 5.25 (dd; 1H: 5ε₁), 5.25 (up; 1H: 5α), 5.30 and 6.15 (2s; 2H:

7.75 (dd; 1H: 1'H₆).

The 5δ-dimethylaminomethylenevirginiamycin S can be prepared as described in Example 2.

EXAMPLE 20

5δ-Dimethylaminomethylenepristinamycin I$_A$ (10.6 g) is added, with stirring, to a 0.1N aqueous solution of hydrochloric acid (420 cc). The solution obtained is then stirred for 3 hours at a temperature of the order of 20° C. A saturated aqueous solution of sodium bicarbonate (30 cc) is then added dropwise so as to obtain a pH of the order of 4. The product which precipitates is filtered off and then washed 3 times with distilled water (30 cc in total). After drying under reduced pressure (2.7 kPa) at a temperature of the order of 20° C., 5δ-hydroxymethylenepristinamycin I$_A$ (9.5 g) is obtained in the form of a beige powder. This product is of sufficient quality to be used as such in the subsequent stages. However, it can be purified in the following manner:

Crude 5δ-hydroxymethylenepristinamycin I$_A$ (9.5 g) is dissolved in ethyl acetate (50 cc) and the solution obtained is poured onto silica gel (100 g) contained in a column of diameter 2.8 cm. Elution is carried out initially with ethyl acetate (400 cc); the corresponding eluate is discarded. Elution is continued with ethyl acetate (1600 cc); the corresponding eluate is concentrated to dryness under reduced pressure (2.7 kPa) at 30° C. This gives 5δ-hydroxymethylenepristinamycin I$_A$ (6.3 g) in the form of white crystals melting at 220° C.

NMR spectrum: 0.69 (dd; 1H: 5β₂), 2.43 (d; 1H: 5β₁), 3.40 (d; 1H: 5ε₂), 4.0 to 4.2 (up; 3H: 4α+5ε₁+5α), 8.15 (s; 1H: =CH—OH), 11.63 (s broad; 1H: =CH—OH).

EXAMPLE 21

Acetyl chloride (0.14 cc) is added, at a temperature of the order of −20° C., to a solution of 5δ-hydroxymethylenepristinamycin I$_A$ (1.8 g) in methylene chloride (20 cc) containing triethylamine (0.2 g), and the temperature is then allowed to rise to about 20° C.

The reaction mixture is subsequently stirred for 20 hours at this temperature and then concentrated to dryness under reduced pressure (2.7 kPa) at 30° C.; the residue obtained is purified by "flash" chromatography [eluent: ethyl acetate]. After concentration to dryness of fractions 4 to 7 under reduced pressure (2.7 kPa) at 30° C., 5δ-acetoxymethylenepristinamycin $I_A$ (0.7 g) is obtained in the form of a yellow powder melting at about 160° C.

NMR spectrum: 0.60 (dd; 1H: 5$\beta_2$), 2.25 (s; 3H: —CO—C$\underline{H}_3$), 2.45 (d; 1H: 5$\beta_1$), 3.45 (dd; 1H: 5$\epsilon_2$), 5.25 (dd; 1H: 5$\alpha$), 5.45 (d; 1H: 5$\epsilon_1$), 7.10 to 7.45 (up; 8H: 6$\gamma$+6$\delta$+6$\epsilon$+1'H$_4$+1'H$_5$+=C$\underline{H}$—O—), 7.85 (dd; 1H: 1'H$_6$).

EXAMPLE 22

By following a procedure analogous to that described in Example 21, but starting from 5δ-hydroxymethylenepristinamycin $I_A$ (1.8 g) and diethyl chlorophosphate (0.34 g), and after purification by "flash" chromatography [eluent: ethyl acetate/methanol (90/10 by volume)] and concentration to dryness of fractions 6 to 14 under reduced pressure (2.7 kPa) at 30° C., 5δ-diethoxyphosphoryloxymethylenepristinamycin $I_A$ (0.8 g) is obtained in the form of a yellow powder melting at about 150° C.

NMR spectrum: 0.55 (dd; 1H: 5$\beta_2$), 1.30 (td; 6H: —PO(O—CH$_2$—C$\underline{H}_3$)$_2$), 2.40 (d; 1H: 5$\beta_1$), 3.40 (dd; 1H: 5$\epsilon_2$), 4.25 (ddd; 4H: —PO(O—C$\underline{H}_2$—CH$_3$)$_2$), 5.25 (d; 1H: 5$\alpha$), 5.40 (d; 1H: 5$\epsilon_1$), 7.10 to 7.55 (up; 8H: 6$\gamma$+6$\delta$+6$\epsilon$+=C$\underline{H}$—O—+1'H$_5$+1'H$_4$), 7.85 (dd; 1H×0.85: 1'H$_6$ 1st isomer), 8 (dd; 1H×0.15: 1'H$_6$ 2nd isomer).

EXAMPLE 23

Triethylamine (0.42 cc) and then p-toluenesulphonyl chloride (0.57 g) are added, at a temperature of the order of −30° C., to a solution of 5δ-hydroxymethylenepristinamycin $I_A$ (2.7 g) in methylene chloride (30 cc) and the temperature is allowed to rise to about 20° C.

The reaction mixture is subsequently stirred for two hours at this temperature and then concentrated to dryness under reduced pressure (2.7 kPa) at 30° C.; the residue obtained is purified by "flash" chromatography [eluent: methylene chloride/methanol (96/4 by volume)]. After concentration to dryness of fractions 4 to 6 under reduced pressure (2.7 kPa) at 30° C., 5δ-(4-methylphenyl)sulphonyloxymethylenepristinamycin $I_A$ (2.2 g) is obtained in the form of a white powder melting at about 265° C.

NMR spectrum: 0.50 (dd; 1H: 5$\beta_2$) 2.35 (s; 3H:

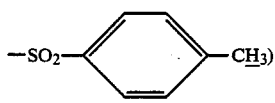

3.30 (dd; 1H: 5$\epsilon_2$) 5.25 (d; 1H: 5$\alpha$) 5.30 (dd; 1H: 5$\epsilon_1$) 7.35 to 7.90 (AB system+up; 8H: 4$\delta$+4$\epsilon$+

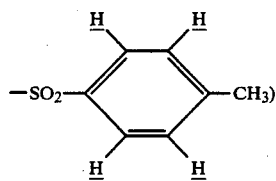

7.85 (dd; 1H: 1'H$_6$)

EXAMPLE 24

A stream of chlorine gas is passed through a solution of triphenyl phosphite (1.3 cc) in methylene chloride (25 cc) until a persistent greenish yellow colour is obtained, the temperature being kept at between −20° C. and −15° C. Triphenyl phosphite (6 drops) is then added in order to decolourize the solution, this being followed by 5δ-hydroxymethylenepristinamycin $I_A$ (4.1 g), the temperature still being kept at between −20° C. and −15° C. The solution obtained is stirred for 1 hour at −15° C. and a solution of pyridine (0.4 cc) in methylene chloride (25 cc) is then added dropwise. The reaction mixture is subsequently stirred for 30 minutes at a temperature of the order of 20° C. and concentrated hydrochloric acid (d=1.19) (0.46 cc) and methylene chloride (50 cc) are then added. The mixture is washed 4 times with distilled water (100 cc in total); the organic phase is dried over magnesium sulphate and filtered and the filtrate is then concentrated to dryness under reduced pressure (2.7 kPa) at 30° C. The residue obtained is purified by "flash" chromatography [eluent: ethyl acetate]; after concentration to dryness of fractions 7 to 9 under reduced pressure (2.7 kPa) at 30° C., 5δ-chloromethylenepristinamycin $I_A$ (1.2 g) is obtained in the form of a beige powder melting at about 190° C.

NMR spectrum: 0.55 (dd; 1H: 5$\beta_2$), 2.45 (d; 1H: 5$\beta_1$), 3.45 (dd; 1H: 5$\epsilon_2$), 5.30 (d; 1H: 5$\alpha$), 5.45 (d; 1H: 5$\epsilon_1$), 7.15 to 7.60 (up; 8H: 6$\gamma$+6$\delta$+6$\epsilon$+1'H$_4$+1'H$_5$+=C$\underline{H}$—Cl), 7.85 (dd; 1H: 1'H$_6$).

APPLICATION EXAMPLE 1

2-Dimethylaminoethylamine (5.3 g) is added dropwise to a solution of 5δ-dimethylaminomethylenepristinamycin $I_A$ (5.5 g) in acetic acid (60 cc) so as not to exceed 25° C. The soltuion obtained is stirred for 20 hours at a temperature of the order of 20° C. and is then poured slowly into a saturated aqueous solution of sodium bicarbonate; the mixture obtained is extracted twice with methylene chloride (750 cc in total). The organic phases are combined, dried over magnesium sulphate and filtered and the filtrate is concentrated to dryness under reduced pressure (2.7 kPa) at 30° C. The residue is purified by "flash" chromatography [eluent: chloroform/methanol (90/10 by volume)]; fractions 10 to 12 are concentrated to dryness under reduced pressure (2.7 kPa) at 30° C. This gives 5δ-(2-dimethylaminoethyl)aminomethylenepristinamycin $I_A$ (3 g) in the form of a beige powder melting at about 180° C.

NMR spectrum: 0.90 (mt; 4H: 2$\gamma$+5$\beta_2$), 2.25 (mt; 6H: —N(CH$_3$)$_2$), 2.50 (mt; 3H: —CH$_2$N<+5$\beta_1$), 3.25 (mt; 2H: —N—CH$_2$—), 3.50 (mt; 2H: 5$\epsilon_2$+3$\delta_1$), 4.90 (mt; 1H: 5$\epsilon_1$), between 7.15 and 7.4 (up; 1H:

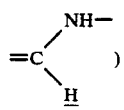

9.90 (mt; 1H (exchangeable with D₂O): —NH—).

A 1% aqueous solution of 5δ-(2-dimethylaminoethyl)aminomethylenepristinamycin I$_A$ (product AG) is obtained with:
product AG . . . 0.1 g
distilled water . . . q.s. 10 cc

APPLICATION EXAMPLE 2

By following a procedure analogous to that described in Application Example 1, but starting from 5δ-dimethylaminomethylenepristinamycin I$_A$ (1.84 g) and 2-diethylaminoethylamine (2.8 cc), and after purification by "flash" chromatography [eluent: chloroform/methanol (96/4 by volume)] and concentration to dryness of fractions 9 to 13 under reduced pressure (2.7 kPa) at 30° C., 5δ-(2-diethylaminoethyl)aminomethylenepristinamycin I$_A$ (1 g) is obtained in the form of a yellow powder melting at about 150° C.

NMR spectrum: 0.9 (mt; 4H: 2γ+5β₂), 1.1 (mt; 6H: —N(CH₂—CH₃)₂), 2.45 (d; 1H: 5β₁), 3.1 to 3.4 (up; 6H:

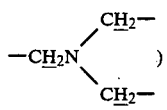

3.50 (mt; 2H: 5ε₂+3δ₁), 4.90 (up; 1H: 5ε₁), 9.9 (up; 1H (exchangeable): =CH—NH—).

A 5% aqueous solution of 5δ-(2-diethylaminoethyl)aminomethylenepristinamycin I$_A$ (product AH) in the form of the hydrochloride is obtained with:
product AH . . . 0.1 g
0.1N hydrochloric acid . . . 1 cc
distilled water . . . q.s. 2 cc

APPLICATION EXAMPLE 3

By following a procedure analogous to that described in Application Example 1, but starting from 5δ-dimethylaminomethylenepristinamycin I$_A$ (2.76 g) and N-methylethylenediamine (2.22 g), and after purification by "flash" chromatography [eluent: chloroform/methanol (95/5 by volume)] and concentration to dryness of fractions 16 to 20 under reduced pressure (2.7 kPa) at 30° C., 5δ-(2-methylaminoethyl)aminomethylenepristinamycin I$_A$ (1.3 g) is obtained in the form of a yellow powder melting at 174° C.

NMR spectrum: 0.90 (up; 4H: 5β₂), 2.50 (up; 1H: 5β₁), 2.7–3.6 (up; 4H: —NH—(CH₂)₂NH—), 3.0 (under unresolved peaks, s; 3H: —NHCH₃), 7.15–7.40 (up; 1H: =CHNH—), 9.90 (up; 1H: =CH—NHCH₃).

A 1% aqueous solution of 5δ-(2-methylaminoethyl)aminomethylenepristinamycin I$_A$ (product AI) in the form of the hydrochloride is obtained with:
product AI . . . 0.03 g
0.1N hydrochloric acid . . . 0.31 cc
distilled water . . . q.s. 3 cc

APPLICATION EXAMPLE 4

By following a procedure analogous to that described in Application Example 1, but starting from 5δ-dimethylaminomethylenepristinamycin I$_A$ (1.84 g) and 3-dimethylaminopropylamine (2.5 cc), and after purification by "flash" chromatography [eluent: chloroform/methanol (90/10 by volume)] and concentration to dryness of fractions 12 to 15 under reduced pressure (2.7 kPa) at 30° C., 5δ-(3-dimethylaminopropyl)aminomethylenepristinamycin I$_A$ (0.7 g) is obtained in the form of a yellow powder melting at about 155° C.

NMR spectrum: 0.80 to 1.05 (mt; 4H: 2γ+5β₂), 1.80 (mt; 2H: —CH₂CH₂—CH₂—), 2.35 (s; 6H×0.85: —N(CH₃)₂ 1st isomer), 2.40 (s; 6H×0.15: —N(CH₃)₂ 2nd isomer), 2.40 to 2.60 (mt; 3H: 5β₁+—CH₂—N>), 3.30 (mt; 2H: —NH—CH₂—), 3.50 (mt; 2H: 3δ₁+5ε₂), 4.90 (mt; 1H: 5ε₁), 9.65 (up; 1H×0.15: =CH—NH— 2nd isomer), 9.90 (up; 1H×0.85: =CH—NH— 1st isomer).

A 6.6% solution of 5δ-(3-dimethylaminopropyl)aminomethylenepristinamycin I$_A$ (product AJ) in the form of the hydrochloride is obtained with:
product AJ . . . 0.1 g
0.2N hydrochloric acid . . . 0.51 cc
distilled water . . . q.s. 1.5 cc

APPLICATION EXAMPLE 5

By following a procedure analogous to that described in Application Example 1, but starting from 5δ-dimethylaminomethylenepristinamycin I$_A$ (2.76 g) and 1-dimethylaminoprop-2-ylamine (3.06 g), and after purification by "flash" chromatography [eluent: chloroform/methanol (99/1 by volume)] and concentration to dryness of fractions 11 to 22 under reduced pressure (2.7 kPa) at 30° C., 5δ-(3-dimethylaminoprop-2-yl)aminomethylenepristinamycin I$_A$ (1.0 g) is obtained in the form of a yellow powder melting at about 160° C.

NMR spectrum: 1.05 (d; 3H:

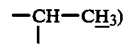

2.30 (s; 6H: —CH₂—N(CH₃)₂), 2.45 (d; 1H: 5β₁), 2.80 (up; 1H:

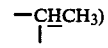

3.30 (under unresolved peaks: —NH—CH₂—), 3.45 (up; 2H: 5ε₂+3δ₁), 4.90 (up; 1H: 5ε₁), 7.15–7.40 (up; 1H: =CHNH—), 9.90 (up; 1H: =CH—NH—).

A 1% aqueous solution of 5δ-(3-dimethylaminoprop-2-yl)aminomethylenepristinamycin I$_A$ (product AK) in the form of the hydrochloride is obtained with:
product AK . . . 20 mg
0.1N hydrochloric acid . . . 0.2 cc
distilled water . . . q.s. 2 cc

APPLICATION EXAMPLE 6

By following a procedure analogous to that described in Application Example 1, but starting from 5δ-dimethylaminomethylenepristinamycin I$_A$ (2.76 g) and 2-dimethylaminopropylamine (1.53 g), and after purification by "flash" chromatography [eluent: chloroform/methanol (95/5 by volume)] and concentration to dryness of fractions 10 to 14 under reduced pressure (2.7 kPa) at 30° C., 5δ-(2-dimethylaminopropyl)aminomethylenepristinamycin I$_A$ (0.85 g) is obtained in the form of an orange powder melting at about 175° C.

NMR spectrum: 0.90 (up; 4H: 2γ+5β₂), 1.05 (d; 3H:

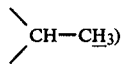

2.30 (s; 6H: —CH(CH₃)N(CH₃)₂), 2.45 (d; 1H; 5β₁), 2.80 (up; 1H:

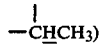

3.30 (under unresolved peaks, 2H: —NH—CH₂—), 3.45 (up; 2H: 5ε₂+3δ₁), 4.90 (up; 1H: 5ε₁), 7.15–7.40 (up; 1H: =CHNH—), 9.90 (up; 1H: =CH—NH—).

A 10% aqueous solution of 5δ-(2-dimethylaminopropyl)aminomethylenepristinamycin I$_A$ (product AL) in the form of the hydrochloride is obtained with:
product AL . . . 0.03 g
0.1N hydrochloric acid . . . 0.31 cc

APPLICATION EXAMPLE 7

By following the procedure analogous to that described in Application Example 1, but starting from 5δ-dimethylaminomethylenepristinamycin I$_A$ (1.84 g) and 2-amino-5-diethylaminopentane (3.16 g), and after purification by "flash" chromatography [eluent: chloroform/methanol (90/10 by volume)] and concentration to dryness of fractions 15 to 27 under reduced pressure (2.7 kPa) at 30° C., 5δ-(5-diethylaminopent-2-yl)aminomethylenepristinamycin I$_A$ (0.9 g) is obtained in the form of a beige powder melting at about 160° C.

NMR spectrum: 1.00 (dd; 1H: 5β₂), 1.25 (mt; 6H: —N(CH₂CH₃)₂), 2.45 (d; 1H: 5β₁), 2.7–3.0 (up; 6H:

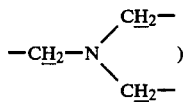

3.45 (dd; 1H: 5ε₂), 7.30 (under the aromatic protons: =CH—NH—), 7.85 (dd; 1H: 1′H₆), 10 (up broad; 1H:

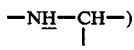

A 1% aqueous solution of 5δ-(5-diethylaminopent-2-yl)aminomethylenepristinamycin I$_A$ (product AM) in the form of the hydrochloride is obtained with:
product AM . . . 0.02 g
0.1N hydrochloric acid . . . 0.2 cc
distilled water . . . q.s. 2 cc

APPLICATION EXAMPLE 8

By following a procedure analogous to that described in Application Example 1, but starting from 5δ-dimethylaminomethylenepristinamycin I$_A$ (1.84 g) and N-(2-aminoethyl)pyrrolidine (2.28 g), and after purification by "flash" chromatography [eluent: chloroform/methanol (98/2 by volume)] and concentration to dryness of fractions 15 to 24 under reduced pressure (2.7 kPa) at 30° C., 5δ-(2-pyrrolidinoethyl)aminomethylenepristinamycin I$_A$ (0.95 g) is obtained in the form of a yellow powder melting at 183° C.

NMR spectrum: 0.90 (mt; 4H: 2γ+5β₂), 1.80 (mt; 4H:

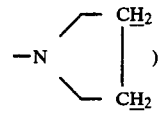

2.70 (mt; 6H:

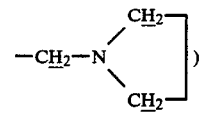

3.45 (up; 4H: —NH—CH₂—+5ε₂+3δ₁), 4.90 (up; 1H: 5ε₁), 7.2–7.4 (up: Ar+1′H₄+1′H₅+CH—), 9.90 (mt; 1H: =CHNHCH₂—).

A 1% solution of 5δ-(2-pyrrolidinoethyl)aminomethylenepristinamycin I$_A$ (product AN) in the form of the hydrochloride is obtained with:
product AN . . . 0.02 g
0.1N hydrochloric acid . . . 0.2 cc
distilled water . . . q.s. 2 cc

APPLICATION EXAMPLE 9

By following a procedure analogous to that described in Application Example 1, but starting from 5δ-dimethylaminomethylenepristinamycin I$_A$ (2.76 g) and N-(3-aminopropyl)pyrrolidine (1.92 g), and after purification by "flash" chromatography [eluent: chloroform/methanol (95/5 by volume)] and concentration to dryness of fractions 10 to 15 under reduced pressure (2.7 kPa) at 30° C., 5δ-(3-pyrrolidinopropyl)aminomethylenepristinamycin I$_A$ (1.25 g) is obtained in the form of a yellow powder melting at 170° C.

NMR spectrum: 0.95 (up; 1H: 5β₂), 1.95 (up; 7H:

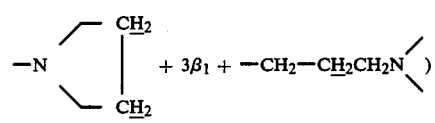

2.45 (d broad; 1H: 5β₁), 2.80 (under unresolved peaks, 6H:

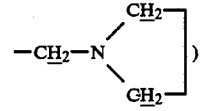

3.30 (mt; 2H: —NH—CH₂—), 3.50 (mt; 2H: 3δ₁+5ε₂), 4.90 (up; 1H: 5ε₁), 7.15–7.40 (up; 1H: =CHNH—), 9.90 (mt; 1H: =CH—N/ —).

A 1% aqueous solution of 5δ-(3-pyrrolidinopropyl)aminomethylenepristinamycin I$_A$ (product AO) is obtained with:
product AO . . . 0.03 g
distilled water . . . 3 cc

APPLICATION EXAMPLE 10

By following a procedure analogous to that described in Application Example 1, but starting from 5δ-dimethylaminomethylenepristinamycin $I_A$ (2.76 g) and N-(2-aminoethyl)piperidine (3.85 g), and after purification by "flash" chromatography [eluent: chloroform/methanol (99/1 by volume)] and concentration to dryness of fractions 13 to 17 under reduced pressure (2.7 kPa) at 30° C., 5δ-(2-piperidinoethyl)aminomethylenepristinamycin $I_A$ (1.5 g) is obtained in the form of a yellow powder melting at about 162° C.

NMR spectrum: 0.90 (up; 4H: $2\gamma + 5\beta_2$), 1.60 (mt; 6H:

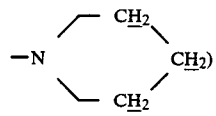

2.40 (up; 6H:

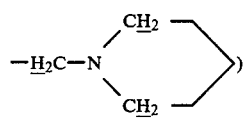

2.7–3.5 (up under unresolved peaks; 2H: —NH—CH$_2$—), 3.45 (mt; 2H: $3\delta_1 + 5\epsilon_2$), 4.90 (mt; 1H: $5\epsilon_1$), 7.15–7.40 (up; 1H: =CHNH—), 9.90 (mt; 1H: =CH—NH—).

A 1% aqueous solution of 5δ-(2-piperidinoethyl)aminomethylenepristinamycin $I_A$ (product AP) in the form of the hydrochloride is obtained with:
product AP . . . 0.02 g
0.1N hydrochloric acid . . . 0.2 cc
distilled water . . . q.s. 2 cc

APPLICATION EXAMPLE 11

By following a procedure analogous to that described in Application Example 1, but starting from N-(2-aminoethyl)morpholine (2.6 g) and 5δ-dimethylaminomethylenepristinamycin $I_A$ (1.84 g), and after purification by "flash" chromatography [eluent: chloroform/methanol (95/5 by volume)] and concentration to dryness of fractions 21 to 30 under reduced pressure (2.7 kPa) at 30° C., 5δ-(2-morpholinoethyl)aminomethylenepristinamycin $I_A$ (0.8 g) is obtained in the form of a beige powder melting at about 172° C.

NMR spectrum: 0.95 (up; 1H: $5\beta_2$), 2.50 (up; 7H: $5\beta_1+$

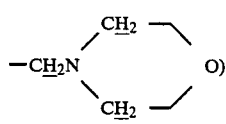

3.30 (up; 2H: —NH—CH$_2$—), 3.50 (up; 2H: $5\epsilon_2 + 3\delta_1$), 3.70 (mt; 4H:

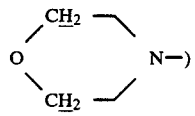

4.90 (up; 1H: $5\epsilon_1$), 7.2–7.4 (up; 1H: =CH—), 9.90 (mt; 1H: =CH—NH—CH$_2$—).

A 1% aqueous solution of 5δ-(2-morpholinoethyl)aminomethylenepristinamycin $I_A$ (product AQ) in the form of the hydrochloride is obtained with:
product AQ . . . 0.02 g
0.1N hydrochloric acid . . . 0.2 cc
distilled water . . . q.s. 2 cc

APPLICATION EXAMPLE 12

By following a procedure analogous to that described in Application Example 1, but starting from 5δ-dimethylaminomethylenepristinamycin $I_A$ (2.76 g) and 2-aminomethyl-1-ethylpyrrolidine (3.66 g), and after purification by "flash" chromatography [eluent: chloroform/methanol (99/1 by volume)] and concentration to dryness of fractions 10 to 14 under reduced pressure (2.7 kPa) at 30° C., 5δ-(1-ethylpyrrolidin-2-yl)methylaminomethylenepristinamycin $I_A$ (1.3 g) is obtained in the form of a beige powder melting at about 160° C.

NMR spectrum: 1.10 (t; 3H: —CH$_2$—CH$_3$), 1.60 (up; 4H:

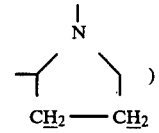

1.95 (up; 1H: =CH—NH—), 2.8–3.6 (up; 4H: —CH$_2$N< +—CH$_2$NH—), 7.15–7.40 (up; 1H: =CHNH—),

A 1% aqueous solution of 5δ-(1-ethylpyrrolidin-2-yl)methylaminomethylenepristinamycin $I_A$ (product AR) in the form of the hydrochloride is obtained with:
product AR . . . 0.02 g
0.1N hydrochloric acid . . . 0.2 cc
distilled water . . . q.s. 2 cc

APPLICATION EXAMPLE 13

By following a procedure analogous to that described in Application Example 1, but starting from 5δ-dimethylaminomethylenepristinamycin $I_A$ (2.77 g) and 3-amino-1-methylpiperidine (3.4 g), and after purification by "flash" chromatography [eluent: chloroform/methanol (95/5 by volume)] and concentration to dryness of fractions 7 to 16 under reduced pressure (2.7 kPa) at 30° C., 5δ-(1-methylpiperidin-3-yl)aminomethylenepristinamycin $I_A$ (0.8 g) is obtained in the form of a beige powder melting at 177° C.

NMR spectrum: 0.90 (mt; 4H: $2\gamma + 5\beta_2$), 1.5–2.10 (mt; 7H: $2\beta_1 + 2\beta_2 + 3\gamma_1 +$

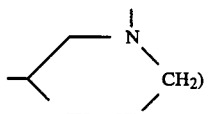

2.30 (s, 3H:

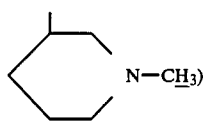

2.45 (d; 1H: 5β₁), 2.65 (mt; 1H:

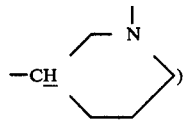

2.90 (mt; 4H: 4β₂+

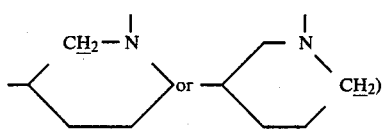

3.20 (mt; 7H: —NCH₃ in the 4-position+3δ₂+4β₁+

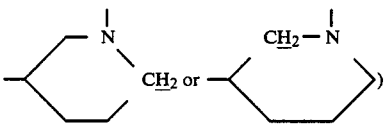

7.15–7.40 (up; 1H: =CHNH—), 7.80 (mt; 1H: 1'H₆), 9.90 (mt; 1H: =CH—NH—), 11.60 (s broad; 1H: OH).

A 1% aqueous solution of 5δ-(1-methylpiperidin-3-yl)aminomethylenepristinamycin I$_A$ (product AS) in the form of the hydrochloride is obtained with:
product AS ... 0.02 g
0.1H hydrochloric acid ... 0.2 cc
distilled water ... q.s. 2 cc The 3-amino-1-methylpiperidine can be prepared according to the method described by L. M. WERBEL, A. CURRY, E. F. ELSLAGER and C. HESS, J. Heterocyclic Chem. 10, 363 (1973).

APPLICATION EXAMPLE 14

By following a procedure analogous to that described in Application Example 1, but starting from 5δ-dimethylaminomethylenepristinamycin I$_A$ (13.8 g) and 4-amino-1-methylpiperidine (3.4 g), and after purification by "flash" chromatography [eluent: chloroform/methanol (92.5/7.5 by volume)] and concentration to dryness of fractions 15 to 20 under reduced pressure (2.7 kPa) at 30° C., 5δ-(1-methylpiperidin-4-yl)aminomethylenepristinamycin I$_A$ (4.0 g) is obtained in the form of a yellow powder melting at 208° C.

NMR spectrum: 0.40 (up; 4H: 2γ+2β₂), 2.0 (up; 4H:

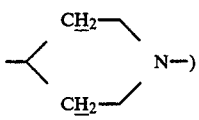

2.35 (s; 3H: >N—CH₃), 2.45 (d, 1H: 5β₁), 2.90

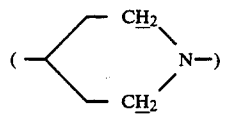

3.20 (under unresolved peaks; 1H:

3.50 (d; 1H: 5ε₂), 4.85 (under unresolved peaks; 1H: 5ε₁), 6.65 (d; 1H: =CHNH—), 9.70 (dd, 1H×0.15: =CH—NH— 1st isomer), 10.03 (dd; 1H×0.85: =CH—NH— 2nd isomer).

A 10% aqueous solution of 5δ-(1-methylpiperidin-4-yl)aminomethylenepristinamycin I$_A$ (product AT) in the form of the hydrochloride is obtained with:
product AT ... 0.03 g
0.1N hydrochloric acid ... 0.3 cc
distilled water ... q.s. 0.3 cc The 4-amino-1-methylpiperidine can be prepared by the method described by E. F. ELSLAGER, L. M. WERBEL, A. CURRY, N. HEADEN and J. JOHNSON, J. Med. Chem. 17, 99 (1974).

APPLICATION EXAMPLE 15

By following a procedure analogous to that described in Application Example 1, but starting from 5δ-dimethylaminomethylenevirginiamycin S (0.8 g) and 4-amino-1-methylpiperidine (1.02 g), and after purification by "flash" chromatography [eluent: chloroform/methanol (90/10 by volume)] and concentration to dryness of fractions 3 to 7 under reduced pressure (2.7 kPa) at 30° C., 5δ-(1-methylpiperidin-4-yl)aminomethylenevirginiamycin S (0.3 g) is obtained in the form of a beige powder melting at about 195° C.

NMR spectrum: 0.9 (up; 4H: 2γ+5β₂), 2.30 (s; 3H:

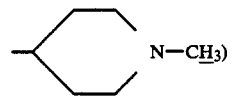

2.80 to 3.30 (up; 5H:

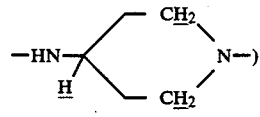

3.55 (dd; 1H: 5ε₂), 4.90 (up; 1H: 5ε₁), 7.10 to 7.40 (up; aromatic protons+=CH—NH—), 7.70 (dd; 1H: 1'H₆), 10.1 (up; 1H: =CH—NH—).

A 5% aqueous solution of 5δ-(1-methylpiperidin-4-yl)aminomethylenevirginiamycin S (product AU) in the form of the hydrochloride is obtained with:
product AU ... 0.1 g
0.1N hydrochloric acid ... 1.05 cc
distilled water ... q.s. 2 cc

APPLICATION EXAMPLE 16

By following a procedure analogous to that described in Application Example 1, but starting from 5δ-dimethylaminomethylenepristinamycin $I_A$ (2.76 g) and 1-(2-aminoethyl)-4-methylpiperazine (2.15 g), and after purification by "flash" chromatography [eluent: chloroform/methanol (95.5 by volume)] and concentration to dryness of fractions 10 to 16 under reduced pressure (2.7 kPa) at 30° C., 5δ-[2-(4-methylpiperazin-1-yl)ethyl]aminomethylenepristinamycin $I_A$ (0.9 g) is obtained in the form of a yellow powder melting at 150° C.

NMR spectrum: 1.00 (up; 1H: $5\beta_2$), 2.30 (s; 3H: >N—CH$_3$), 2.50 (up; 9H: —CH$_2$-piperazine+$5\beta_1$), 2.90 (under unresolved peaks: —CH$_2$CH$_2$—N<), 3.30 (up; 2H: —NH—CH$_2$—), 3.50 (up; 2H: $\overline{5\epsilon_2+3\delta_1}$), 4.90 (up; 1H: $5\epsilon_1$), 7.15–7.40 (up; 1H: =CHNH—), 9.90 (up; 1H: =CH—NH—).

A 10% aqueous solution of 5δ-[2-(4-methylpiperazin-1-yl)ethyl]aminomethylenepristinamycin $I_A$ (product AV) in the form of the hydrochloride is obtained with:
product AV . . . 15 mg
0.1N hydrochloric acid . . . 0.15 cc The 1-(2-aminoethyl)-4-methylpiperazine can be prepared in the following manner:

N-Methylpiperazine (9.75 g) is added to a solution of 2-bromoethylamine hydrobromide (10.0 g) in absolute ethanol (60 cc). The solution obtained is stirred for 16 hours at a temperature of the order of 20° C. and the ethanol is then removed under reduced pressure (2.7 kPa) at 30° C. The oily residue is taken up with chloroform (50 cc); the mixture obtained is stirred with a 10N aqueous solution of sodium hydroxide (20 cc). The aqueous phase is extracted 3 times with chloroform (150 cc in total). The organic phases are combined, dried over sodium sulphate and filtered and the filtrate is concentrated to dryness under reduced pressure (2.7 kPa) at 30° C. The residue is distilled under reduced pressure (2.7 kPa); this gives 1-(2-aminoethyl)-4-methylpiperazine (4.5 g) in the form of a yellow oil [b.p. (2.7 kPa)=118°–119° C.].

APPLICATION EXAMPLE 17

By following a procedure analogous to that described in Application Example 1, but starting from 5δ-dimethylaminomethylenepristinamycin $I_A$ (4.0 g) and histamine (0.55 g), and after purification by "flash" chromatography [eluent: chloroform/methanol (95/5 by volume)] and concentration to dryness of fractions 25 to 50 under reduced pressure (2.7 kPa) at 30° C., 5δ-[2-(imidazol-4-yl)ethyl]aminomethylenepristinamycin $I_A$ (2.04 g) is obtained in the form of a yellow powder melting at 138° C.

NMR spectrum: 0.90 (up; 4H: $2\gamma+5\beta_2$), 2.40 (d broad; 1H: $5\beta_1$), 2.90 (under unresolved peaks, up; 1H: $5\epsilon_1$), 3.50 (d; 4H: $5\epsilon_2+3\delta_1+$—NH—CH$_2$—), 4.80 (under unresolved peaks, 1H: $5\epsilon_1$), 6.65 (up; 2H: H$_5$+>NH histamine), 7.50 (s; 1H, H in the 2-position of the histamine), between 7.15 and 7.40 (up; 1H: =CHNH—), 9.65 (up; 1H×0.15: =CH—NH— 2nd isomer), 9.95 (up; 1H×0.85: =CH—NH— 1st isomer).

A 10% aqueous solution of 5δ-[2-(imidazol-4-yl)ethylaminomethylene]pristinamycin $I_A$ (product AW) in the form of the hydrochloride is obtained with:
product AW . . . 0.1 g
0.1N hydrochloric acid . . . q.s. 1 cc

APPLICATION EXAMPLE 18

2-Dimethylaminoethanethiol (2.1 g) is added to a solution of 5δ-dimethylaminomethylenepristinamycin $I_A$ (1.84 g) in acetic acid (40 cc). The solution obtained is stirred for 20 hours at a temperature of the order of 20° C. and is then poured slowly into a saturated aqueous solution of sodium bicarbonate; the mixture obtained is extracted 3 times with methylene chloride (400 cc in total). The organic phases are combined, dried over magnesium sulphate and filtered and the filtrate is concentrated to dryness under reduced pressure (2.7 kPa) at 30° C. The residue obtained is purified by "flash" chromatography [eluent: chloroform/methanol (96/4 by volume)]; fractions 5 and 6 are combined and concentrated to dryness under reduced pressure (2.7 kPa) at 30° C. This gives 5δ-(2-dimethylaminoethyl)thiomethylenepristinamycin $I_A$ (0.8 g) in the form of a yellow powder melting at about 150° C.

NMR spectrum: 0.68 (dd; 1H: $5\beta_2$), 2.32 (s; 6H×0.85: —CH$_2$N(CH$_3$)$_2$ 1st isomer), 2.35 (s; 6H×0.15: —CH$_2$N(CH$_3$)$_2$ 2nd isomer), 2.45 (d; 1H×$5\beta_1$), 2.65 (mt; 2H: —SCH$_2$—), 3.05 (t; 2H: —CH$_2$N<), 3.43 (dd; 1H: $5\epsilon_2$), 5.15 (in unresolved peaks: $5\epsilon_1$), 7.60 (s broad; 1H: =CHS—), 7.83 (mt; 1H: 1'H$_6$ two isomers).

A 1% aqueous solution of 5δ-(2-dimethylaminoethyl)thiomethylenepristinamycin $I_A$ (product AX) in the form of the hydrochloride is obtained with:
product AX . . . 0.1 g
0.1N hydrochloric acid . . . 1 cc
distilled water . . . q.s. 10 cc

APPLICATION EXAMPLE 19

By following a procedure analogous to that described in Application Example 18, but starting from 5δ-dimethylaminomethylenepristinamycin $I_A$ (3.68 g) and 2-diethylaminoethanethiol (8.5 g), and after purification by "flash" chromatography [eluent: chloroform/methanol (96/4 by volume)] and concentration to dryness of fractions 13 to 20 under reduced pressure (2.7 kPa) at 30° C., 5δ-(2-diethylaminoethyl)thiomethylenepristinamycin $I_A$ (0.85 g) is obtained in the form of a beige powder melting at about 192° C.

NMR spectrum: 0.65 (dd; 1H: $5\beta_2$), 1.05 (t; 6H: —N(CH$_2$CH$_3$)$_2$), 2.42 (d; 1H: $5\beta_1$), 2.60 (q; 4H: —N(CH$_2$CH$_3$)$_2$), 3.42 (dd; 1H: $5\epsilon_2$), 5.10 (under unresolved peaks, 1H: $5\epsilon_1$), 7.58 (s broad; 1H: =CH—S—), 7.82 (dd; 1H×0.95: 1'H$_6$ 1st isomer), 7.98 (dd; $\overline{1H}$×0.05: 1'H$_6$ 2nd isomer).

A 1% aqueous solution of 5δ-(2-diethylaminoethyl)thiomethylenepristinamycin $I_A$ (product AY) in the form of the hydrochloride is obtained with:
product AY . . . 0.04 g
0.1N hydrochloric acid . . . 0.4 cc
distilled water . . . q.s. 4 cc

APPLICATION EXAMPLE 20

By following a procedure analogous to that described in Application Example 18, but starting from 5δ-dimethylaminomethylenepristinamycin $I_A$ (3 g) and 3-dimethylaminopropanethiol (0.4 g), and after purification by "flash" chromatography [eluent: chloroform/methanol (92.5/7.5 by volume)] and concentration to dryness of fractions 10 to 17 under reduced pressure (2.7 kPa) at 30° C., 5δ-(3-dimethylaminopropyl)thiomethylenepristinamycin $I_A$ (0.85 g) is obtained in the form of a beige powder melting at about 170° C.

NMR spectrum: 0.70 (dd; 1H: 5β₂) 1.90 (up; 2H: —S—CH₂CH₂CH₂N<) 2.20 (s; 6H: —N(CH₃)₂) 2.40 (d; 1H: 5β₁) 2.90 (up; 2H: —CH₂—N<) 3.45 (dd; 1H: 5ε₂) 7.65 (s broad; 1H: =CH—S—)

A 1% aqueous solution of 5δ-(3-dimethylaminopropyl)thiomethylenepristinamycin I$_A$ (product AZ) in the form of the hydrochloride is obtained with:
product AZ ... 0.03 g
0.1N hydrochloric acid ... 0.3 cc
distilled water ... q.s. 3 cc

APPLICATION EXAMPLE 21

By following a procedure analogous to that described in Application Example 18, but starting from 5δ-dimethylaminomethylenevirginiamycin S (1.8 g) and 3-dimethylaminopropanethiol (0.48 g), and after purification by "flash" chromatography [eluent: chloroform/methanol (95/5 by volume)] and concentration to dryness of fractions 5 to 14 under reduced pressure (2.7 kPa) at 30° C., 5δ-(3-dimethylaminopropyl)thiomethylenevirginiamycin S (0.7 g) is obtained in the form of a beige powder melting at about 140° C.

NMR spectrum: 0.50 (dd; 1H: 5β₂), 2 (up; 2H: —SCH₂CH₂—CH₂N<), 2.35 (s; 6H: —S(CH₂)₃N(CH₃)₂), 2.60 (t; 2H: —SCH₂—CH₂CH₂—N<), 3(t; 2H: —SCH₂CH₂CH₂N<), 3.35 (dd; 1H: 5ε₂), 4.90 (dd; 1H: 5ε₁), 5.20 (up; 1H: 5α), 7.60 (s broad; 1H: =CH—S—), 7.80 (dd; 1H: 1'H₆).

A 10% aqueous solution of 5δ-(3-dimethylaminopropyl)thiomethylenevirginiamycin S (product AAA) in the form of the hydrochloride is obtained with:
product AAA ... 0.1 g
0.2N hydrochloric acid ... 0.52 cc
distilled water ... q.s. 1 cc

APPLICATION EXAMPLE 22

By following a procedure analogous to that described in Application Example 18, but starting from 5δ-dimethylaminomethylenepristinamycin I$_A$ (4 g) and 3-dimethylamino-2-methylpropanethiol (0.7 g), and after purification by "flash" chromatography [eluent: chloroform/methanol (94.6 by volume)] and concentration to dryness under reduced pressure (2.7 kPa) at 30° C., 5δ-(3-dimethylamino-2-methylpropyl)thiomethylenepristinamycin I$_A$ (0.96 g) is obtained in the form of a beige powder melting at 234° C.

NMR spectrum: 0.65 (dd; 1H: 5β₂), 1.05 (d; 3H:

2.25 (s; 6H: —N(CH₃)₂), 2.40 (d; 1H: 5β₁), 3.15 and 2.90 (ABX system, 2H: —CH₂N<), 3.45 (d broad; 2H: 5ε), 7.75 (dd; 1H×0.80: 1'H₆ 1st isomer), 7.95 (dd; 1H×0.20: 1'H₆ 2nd isomer).

A 1% aqueous solution of 5δ-(3-dimethylamino-2-methylpropyl)thiomethylenepristinamycin I$_A$ (product AAB) in the form of the hydrochloride is obtained with:
product AAB ... 0.03 g
0.1N hydrochloric acid ... 0.3 cc
distilled water ... q.s. 3 cc The 3-dimethylamino-2-methylpropanethiol can be prepared in the following manner:

Sodium (0.026 g) is added to a solution of N,N-dimethyl-3-acetylthio-2-methylpropylamine (5.33 g) in anhydrous methanol (50 cc). The mixture obtained is heated under reflux for 7 hours and the methanol is then removed under reduced pressure (2.7 kPa) at 50° C. The residue is distilled under reduced pressure (2.7 kPa). This gives 3-dimethylamino-2-methylpropanethiol (0.9 g) in the form of a yellow oil distilling at 56° C. under 2.7 kPa.

The N,N-dimethyl-3-acetylthio-2-methylpropylamine can be prepared in the following manner:

Thiolacetic acid (15.7 cc) is added to a solution of N,N-dimethyl-1-chloro-2-methylpropylamine (29.5 g) in isopropanol (120 cc). The mixture obtained is heated under reflux for 48 hours and the isopropanol is then removed under reduced pressure (2.7 kPa) at 60° C. The residue obtained is treated with a saturated aqueous solution of sodium bicarbonate (100 cc) and the aqueous phase is extracted 3 times with ethyl ether (600 cc in total). The organic phases are combined, dried over magnesium sulphate and filtered and the filtrate is concentrated to dryness. The residue obtained is purified by "flash" chromatography [eluent: chloroform/methanol (90/10 by volume)]; fractions 6 to 10 are combined and concentrated to dryness under reduced pressure (2.7 kPa) at 30° C. This gives N,N-dimethyl-3-acetylthio-2-methylpropylamine (5.57 g) in the form of a red oil.

The N,N-dimethyl-1-chloro-2-methylpropylamine can be prepared according to the method described by J. P. BOURQUIN et al., Helv. Chim. Acta, 41, 1072 (1958).

APPLICATION EXAMPLE 23

By following a procedure analogous to that described in Application Example 18, but starting from 5δ-dimethylaminomethylenepristinamycin I$_A$ (4 g) and 2-dimethylamino-2-methylpropanethiol (1.14 g), and after purification by "flash" chromatography [eluent: chloroform/methanol (92/8 by volume)] and concentration to dryness of fractions 12 to 30 under reduced pressure (2.7 kPa) at 30° C., 5δ-(2-dimethylamino-2-methylpropyl)thiomethylenepristinamycin I$_A$ (1.4 g) is obtained in the form of a beige powder melting at about 200° C.

NMR spectrum: 0.55 (dd; 1H×0.20: 5β₂ 2nd isomer), 0.68 (dd; 1H×0.80: 5β₂ 1st isomer), 1.15 (s, 6H: —C(CH₃)₂—), 2.30 (s; 6H×0.80: —N(CH₃)₂ 1st isomer), 2.42 (s; 6H×0.20: —N(CH₃)₂ 2nd isomer), 2.40 (d; 1H: 5β₁), 2.80 (under unresolved peaks: —S—CH₂—), 3.42 (dd; 1H: 5ε₂), 7.55 (s broad: 1H: =CH—S), 7.80 (dd; 1H×0.80: 1'H₆ 1st isomer), 7.98 (dd; 1H×0.20: 1'H₆ 2nd isomer).

A 1% aqueous solution of 5δ-(2-dimethylamino-2-methylpropyl)thiomethylenepristinamycin I$_A$ (product AAC) in the form of the hydrochloride is obtained with:
product AAC ... 0.03 mg
hydrochloric acid ... 0.3 ml
distilled water ... q.s. 3 ml The 2-dimethylamino-2-methylpropanethiol can be prepared according to themethod described by H. R. SNYDER, J. M. STEWART and J. B. ZIEGLER, J. Am. Chem. Soc., 69, 2672 (1947).

APPLICATION EXAMPLE 24

By following a procedure analogous to that described in Application Example 18, but starting from 5δ-dimethylaminomethylenepristinamycin I$_A$ (4 g) and 2-(pyrrolidin-1-yl)ethanethiol (1.1 g), and after purification by "flash" chromatography [eluent: chloroform/methanol (96/4 by volume)] and concentration to dryness of fractions 9 to 15 under reduced pressure (2.7 kPa) at 30° C., 5δ-[2-(pyrrolidin-1-yl)ethyl]thiomethylene-pristinamycin I$_A$ (1.3 g) is obtained in the form of a beige powder melting at about 180° C.

NMR spectrum: 0.65 (dd; 1H: 5β$_2$), 1.85 (up; 4H:

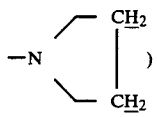

2.45 (d; 1H: 5β$_1$), 2.75 and 2.90 (up; 8H:

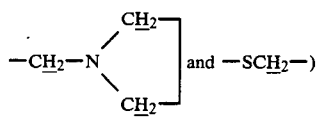

3.45 (dd; 1H: 5ε$_2$),
7.60 (s broad; 1H: =CH—S—) 7.85 (dd; 1H: 1'H$_6$)

A 1% aqueous solution of 5δ-[2-(pyrrolidin-1-yl)ethyl]thiomethylenepristinamycin I$_A$ (product AAD) in the form of the hydrochloride is obtained with:
product AAD ... 0.03 g
0.1N hydrochloric acid ... 0.3 ml
distilled water ... q.s. 3 ml The 2-(pyrrolidin-1-yl)ethanethiol can be prepared according to the method described by J. W. HAEFFELE and R. W. BROGE, Proc. Sci. Toilet Goods Assoc. 32, 52 (1959) [Chem. Abstr. 54, 17234e (1960)].

APPLICATION EXAMPLE 25

By following a procedure analogous to that described in Application Example 18, but starting from 5δ-dimethylaminomethlenepristinamycin I$_A$ (4 g) and 2-(1-methylpyrrolidin-2-yl)ethanethiol (1.74 g), and after purification by "flash" chromatography [eluent: chloroform/methanol (92/8 by volume)] and concentration to dryness of fractions 12 to 22 under reduced pressure (2.7 kPa) at 30° C., 5δ-[2-(1-methylpyrrolidin-2-yl)ethyl]thiomethylenepristinamycin I$_A$ (1.33 g) is obtained in the form of a beige powder melting at about 215° C.

NMR spectrum: 0.65 (dd; 1H: 5β$_2$) 1.4–2.3 (up; 6H:

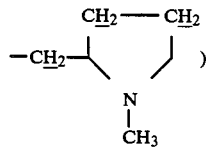

2.40 (d; 1H: 5β$_1$), 2.48 (s; 3H: >N—CH$_3$ pyrrolidine), 3.40 (dd; 1H: 5ε$_2$), 7.50 (s broad; 1H: =CH—), 7.80 (dd; 1H×0.85: 1'H$_6$ 1st isomer), 8.00 (dd; 1H×0.15: 1'H$_6$ 2nd isomer).

A 0.6% aqueous solution of 5δ-[2-(1-methylpyrrolidin-2-yl)ethyl]thiomethylenepristinamycin I$_A$ (product AAE) in the form of the hydrochloride is obtained with:
product AAE ... 0.03 g
0.1N hydrochloric acid ... 0.3 cc
distilled water ... q.s. 5 cc The 2-(1-methylpyrrolidin-2-yl)ethanethiol can be prepared by a procedure analogous to that described in Application Example 22 for preparing 3-dimethylamino-2-methylpropanethiol, but starting from 2-(2-acetylthioethyl)-1-methylpyrrolidine (15.7 g) and sodium (0.07 g). This gives a product (12.2 g) in the form of a red oil.

The 2-(2-acetylthioethyl)-1-methylpyrrolidine can be prepared by a procedure analogous to that described in Application Example 22 for preparing N,N-dimethyl-3-acetylthio-2-methylpropylamine, but starting from 2-(2-chloroethyl)-1-methylpyrrolidine (12.7 g) and thiolacetic acid (6.8 cc). This gives a product (15.7 g) in the form of a red oil.

APPLICATION EXAMPLE 26

By following a procedure analogous to that described in Application Example 18, but starting from 5δ-dimethylaminomethylenepristinamycin I$_A$ (3.0 g) and 4-mercapto-1-methylpiperidine (0.48 g), and after purification by "flash" chromatography [eluent: chloroform/methanol (90/10 by volume)] and concentration to dryness of fractions 15 to 19 under reduced pressure (2.7 kPa) at 30° C., 5δ-(1-methylpiperidin-4-yl)thiomethylenepristinamycin I$_A$ (1.2 g) is obtained in the form of a yellow powder melting at about 170° C.

NMR spectrum: 0.68 (dd; 1H: 5β$_2$), 2.0–2.2 (up; 4H:

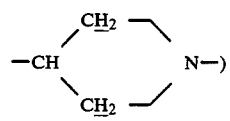

2.30 (s; 3H: >N—CH$_3$), 2.45 (d; 1H: 5β$_1$), 2.85 (up; 4H:

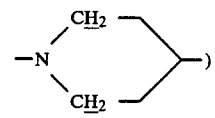

3.05 (mt; 1H:

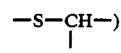

3.40 (dd; 1H: 5ε$_2$), 5.15 (d; 1H: 5ε$_1$), 7.67 (s broad; 1H: =CH—S—), 7.85 (dd; 1H×0.85: 1'H$_6$ 1st isomer), 8.0 (dd; 1H×0.15: 1'H$_6$ 2nd isomer).

A 1% aqueous solution of 5δ-(1-methylpiperidin-4-yl)thiomethylenepristinamycin I$_A$ (Product AAF) in the form of the hydrochloride is obtained with:
product AAF ... 0.05 g
0.1N hydrochloric acid ... 0.5 cc
distilled water ... q.s. 5 cc The 4-mercapto-1-methylpiperidine can be prepared according to the method described by H. BARRER and R. E. LYLE, J. Org. Chem. 27, 641 (1962).

APPLICATION EXAMPLE 27

By following a procedure analogous to that described in Application Example 18, but starting from 5δ-dimethylaminomethylenepristinamycin I$_A$ (4 g) and 1-ethyl-3-mercaptopiperidine (0.8 g), and after purification by "flash" chromatography [eluent: chloroform/methanol (92/8 by volume)] and concentration to dryness of fractions 6 to 9 under reduced pressure (2.7 kPa) at 30° C., 5δ-(1-ethylpiperidin-3-yl)thiomethylenepristinamycin I$_A$ (1.1 g) is obtained, which melts at about 175° C.

NMR spectrum: 0.70 (s broad, 1H: 5β₂), 1.20 (t; 3H: —CH₂CH₃), 2.45 (d broad; 1H: 5β₁), 2.90 (up; 6H:

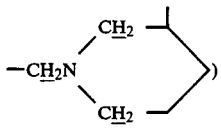

7.50 (s broad; 1H: =CH—S—), 7.80 (dd; 1H×0.80: 1'H₆ 1st isomer), 7.95 (dd; 1H×0.20: 1'H₆ 2nd isomer).

A 1% aqueous solution of 5δ-(1-ethylpiperidin-3-yl)thiomethylenepristinamycin I$_A$ (product AAG) in the form of the hydrochloride is obtained with:
product AAG ... 0.03 g
0.1N hydrochloric acid ... 0.3 cc
distilled water ... q.s. 3 cc The 1-ethyl-3-mercaptopiperidine can be prepared according to the method described by J. H. BIEL et al., J. Am. Chem. Soc. 77, 2250 (1955).

APPLICATION EXAMPLE 28

By following a procedure analogous to the described in Application Example 18, but starting from 5δ-dimethylaminomethylenepristinamycin I$_A$ (3.0 g) and N-(2-mercaptoethyl)-N,N',N'-trimethylethylenediamine (0.55 g), and after purification by "flash" chromatography [eluent: chloroform/methanol (90/10 by volume)] and concentration to dryness of fractions 17 to 24 under reduced pressure (2.7 kPa) at 30° C., 5δ-[2-(2-dimethylaminoethyl)methylaminoethyl]thiomethylenepristinamycin I$_A$ (1.0 g) is obtained in the form of a yellow powder melting at about 160° C.

NMR spectrum: 0.68 (dd; 1H: 5β₂), 2.30 (s; 3H:

2.40 (d; 1H: 5β₁), 2.4–3.1 (up; 8H: —S(CH₂)₂N—(CH₂)₂N<), 3.40 (dd; 1H: 5ε₂), 5.10 (under unresolved peaks; 1H: 5ε₁), 7.58 (s broad; 1H: =CH—S—), 7.80 (dd; 1H: 1'H₆).

A 1% aqueous solution of 5δ-[2-(2-dimethylaminoethyl)methylaminoethyl]thiomethylenepristinamycin I$_A$ (product AAH) is obtained with:
product AAH ... 0.03 g
distilled water ... q.s. 3 cc The N-(2-mercaptoethyl)-N,N',N'-trimethylethylenediamine can be prepared in the following manner: ethyl 2-mercaptoethyl carbonate (5.0 g) is added to a solution of N,N',N'-trimethylethylenediamine (10.2 g) in toluene (40 cc), heated under reflux. After 5 hours under reflux, the toluene is removed under reduced pressure (2.7 kPa) at 50° C. and the residue is distilled at this pressure. This gives N-(2-mercaptoethyl)-N,N',N'-trimethylethylenediamine in the form of a yellow liquid distilling at 105° C. under 2.7 kPa.

The ethyl 2-mercaptoethyl carbonate can be prepared according to the method described by D. D. REYNOLDS, D. L. FIELDS and D. L. JOHNSON, J. Org. Chem., 26, 5125 (1961).

APPLICATION EXAMPLE 29

By following a procedure analogous to that described in Application Example 18, but starting from 5δ-dimethylaminomethylenepristinamycin I$_A$ (4 g) and 1,3-bis(-dimethylamino)propane-2-thiol (2 g), and after purification by "flash" chromatography [eluent: chloroform/methanol (92/8 by volume)] and concentration to dryness of fractions 32 to 56 under reduced pressure (2.7 kPa) at 30° C., 5δ-[1,3-bis(dimethylamino)prop-2-yl]thiomethylenepristinamycin I$_A$ (1.6 g) is obtained in the form of a beige powder melting at about 190° C.

NMR spectrum: 0.55 (dd; 1H×0.80: 5β₂ 2nd isomer), 0.67 (dd; 1H×0.20: 5β₂ 1st isomer), 2.30 (up; 6H: —N(CH₃)₂), 2.8–3.2 (up; 4H: —SCH(CH₂N<)₂), 7.62 (up; 1H: =CH—S—), 7.80 (dd; 1H×0.80: 1'H₆ 1st isomer), 7.98 (dd; 1H×0.20: 1'H₆ 2nd isomer).

A 1% aqueous solution of 5δ-[1,3-bis(dimethylamino)prop-2-yl]thiomethylenepristinamycin I$_A$ (product AAI) in the form of the hydrochloride is obtained with:
product AAI ... 0.03 g
0.1N hydrochloric acid ... 0.3 cc
distilled water ... q.s. 3 cc The 1,3-bis(dimethylamino)propane-2-thiol can be prepared according to the method described by J. M. Stewart, J. Org. Chem., 29, 1655 (1964).

APPLICATION EXAMPLE 30

By following a procedure analogous to that described in Application Example 18, but starting from 5δ-dimethylaminomethylenepristinamycin I$_A$ (3.0 g) and 1-(2-mercaptoethyl)-4-methylpiperazine (0.58 g), and after purification by "flash" chromatography [eluent: chloroform/methanol (87.5/12.5 by volume)] and concentration to dryness of fractions 16 to 30 under reduced pressure (2.7 kPa) at 30° C., 5δ-[2-(4-methylpiperazin-1-yl)ethyl]thiomethylenepristinamycin I$_A$ (1.6 g) is obtained in the form of a beige powder melting at about 170° C.

NMR spectrum: 0.56 (dd; 1H×0.20: 5β₂ 1st isomer), 0.68 (dd; 1H×0.80: 5β₂ 2nd isomer), 2.40 (s; 3H: >NCH₃), 2.5–3 (up; 12H: —S(CH₂)₂N<+all the —CH₂— of piperazine), 3.42 (dd; 1H: 5ε₂), 5.12 (d broad: 5ε₁), 7.60 (s broad; 1H: =CHS—), 7.80 (dd; 1H: 1'H₆, mixture of the 2 isomers).

A 1% aqueous solution of 5δ-[2-(4-methylpiperazin-1-yl)ethyl]thiomethylenepristinamycin I$_A$ (product AAJ) in the form of the hydrochloride is obtained with:
product AAJ ... 0.05 g
0.1N hydrochloric acid ... 0.5 cc
distilled water ... q.s. 5 cc The 1-(2-mercaptoethyl)-4-methylpiperazine can be prepared according to the method described by D. D. REYNOLDS et al., J. Org. Chem. 26, 5125 (1961).

APPLICATION EXAMPLE 31

By following a procedure analogous to that described in Application Example 18, but starting from 5δ-dimethylaminomethylenepristinamycin I$_A$ (4.0 g) and 1-(3-mercaptopropyl)-4-methylpiperazine (1.5 g), and after purification by "flash" chromatography [eluent: chloroform/methanol (95/5 by volume)] and concentration to dryness of fractions 24 to 41 under reduced pressure (2.7 kPa) at 30° C., 5δ-[3-(4-methylpiperazin-1-yl)propyl]thiomethylenepristinamycin I$_A$ (2.06 g) is obtained in the form of a beige powder melting at about 190° C.

NMR spectrum: 0.68 (dd; 1H: 5β₂), 1.90 (mt; 2H: —CH₂—CH₂CH₂N<), 2.40 (s; 3H: >NCH₃), 2.3 to 2.8 (up; 8H: —S—CH₂—+—CH₂

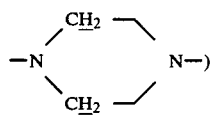

3.45 (up; 1H: 5ε₂), 7.64 (s broad; 1H×0.80: =CH—S— 1st isomer), 7.70 (s broad; 1H×0.20: =CH—S— 2nd isomer), 7.80 (dd; 1H×0.80: 1'H₆ 1st isomer), 7.98 (dd; 1H×0.20: 1'H₆ 2nd isomer).

A 10% aqueous solution of 5δ-[3-(4-methylpiperazin-1-yl)propyl]thiomethylenepristinamycin $I_A$ (product AAK) in the form of the hydrochloride is obtained with:
product AAK ... 0.05 g
0.1N hydrochloric acid ... q.s. 0.5 ml The 1-(3-mercaptopropyl)-4-methylpiperazine can be prepared in a manner analogous to that described in Application Example 22 for preparing 3-dimethylamino-2-methylpropanethiol, but starting from 1-(3-acetylthiopropyl)-4-methylpiperazine (109 g) and sodium (0.46 g). This gives 1-(3-mercaptopropyl)-4-methylpiperazine (64.8 g) in the form of a yellow oil distilling at 133° C. under 0.13 kPa.

The 1-(3-acetylthiopropyl)-4-methylpiperazine can be prepared in a manner analogous to that described in Application Example 22 for preparing N,N-dimethyl-3-acetylthio-2-methylpropylamine, but starting from 1-(3-chloropropyl)-4-methylpiperazine (138 g) and thiolacetic acid (68.5 g). This gives 1-(3-acetylthiopropyl)-4-methylpiperazine (109 g) in the form of a yellow oil distilling at about 160° C. under 0.13 kPa.

APPLICATION EXAMPLE 32

By following a procedure analogous to that described in Application Example 18, but starting from 5δ-dimethylaminomethylenepristinamycin $I_A$ (4.0 g) and 3-mercapto-2-methylpropylammonium iodide (1.3 g), and after purification by "flash" chromatography [eluent: chloroform/methanol (80/20 by volume)] and concentration to dryness of fractions 12 to 22 under reduced pressure (2.7 kPa) at 30° C., 5δ-(2-methyl-3-trimethylammoniopropyl)thiomethylenepristinamycin $I_A$ iodide (1.05 g) is obtained in the form of an ochre powder melting at about 150° C.

NMR spectrum: 1.05–1.35 (up; 8H: 1γ+3γ₂+3β+

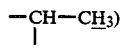

2.40 (up; 2H: 5β₁+

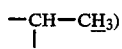

2.90 (mt; 3H: 4β₂+—S—CH₂—), 3.20 (mt; 7H: 4NCH₃+4β₁+3δ₁+—C$\underline{H}$₂⊕N(CH₃)₃), 3.40 (mt; 9H: —N⊕(C$\underline{H}$₃)₃).

A 1% aqueous solution of 5δ-(2-methyl-3-trimethylammoniopropyl)thiomethylenepristinamycin $I_A$ iodide (product AAL) in the form of the hydrochloride is obtained with:
product AAL ... 0.02 g
0.1N hydrochloric acid ... 0.2 cc
distilled water ... q.s. 2 cc The 3-mercapto-2-methylpropylammonium iodide can be prepared in the following manner: sodium methylate (0.024 g) is added to a solution of 3-acetylthio-2-methylpropylammonium iodide (3.6 g) in methanol (18 cc) at a temperature of the order of 20° C. The mixture obtained is heated under reflux for 1 hour and then left at ambient temperature for 16 hours. The methanol is removed under reduced pressure (2.7 kPa) at 50° C. The residue is stirred for 1 hour with isopropanol (35 cc), the white suspension is filtered and the material on the filter is then dried. This gives 3-mercapto-2-methylpropylammonium iodide (3.1 g) in the form of a beige powder melting at 120° C.

The 3-acetylthio-2-methylpropylammonium iodide can be prepared in the following manner: methyl iodide (1.4 cc) is added to a solution of N,N-dimethyl-3-acetylthio-2-methylpropylamine (3.5 g) in acetonitrile (35 cc); after stirring for 18 hours at a temperature of the order of 20° C., the precipitate is filtered off and then dried. This gives 3-acetylthio-2-methylpropylammonium iodide (3.8 g) in the form of a white powder melting at 181° C.

APPLICATION EXAMPLE 33

By following a procedure analogous to that described in Application Example 18, but starting from 5δ-dimethylaminomethylenepristinamycin $I_A$ (1.84 g) and the sodium salt of 2-mercaptoethanesulphonic acid (3.28 g), and after purification by "flash" chromatography [eluent: methylene chloride/methanol (90/10 by volume)] and concentration to dryness of fractions 6 to 14 under reduced pressure (2.7 kPa) at 30° C., 5δ-(2-hydroxysulphonylethyl)thiomethylenepristinamycin $I_A$ (0.8 g) is obtained in the form of a yellow powder melting at a temperature above 280° C.

The infra-red spectrum contains the bands characteristic of pristinamycins: 1745, 1680, 1650, 1525, 815, 740 and 705 cm⁻¹, plus the bands characteristic of the group —SO₃H [1200 cm⁻¹ (broad) and 1050 cm⁻¹].

A 5% aqueous solution of 5δ-(2-hydroxysulphonylethyl)thiomethylenepristinamycin $I_A$ (product AAM) is obtained with:
product AAM ... 0.1 g
distilled water ... q.s. 2 cc

APPLICATION EXAMPLE 34

A solution of 5δ-(4-methylphenyl)sulphonyloxymethylenepristinamycin $I_A$ (5.2 g) in methylene chloride (50 cc) is added to a solution of 1-(2-mercaptopropyl)-4-methylpiperazine (0.87 g) in ethanol (50 cc), to which sodium ethylate (0.34 g) has been added. The reaction mixture is stirred for 16 hours at a temperature of the order of 20° C. and then diluted with methylene chloride (500 cc) and distilled water (100 cc). After stirring, the aqueous phase is extracted twice with methylene chloride (50 cc in total). The organic phases are combined, dried over magnesium sulphate and filtered and the filtrate is then concentrated to dryness under reduced pressure (2.7 kPa) at 30° C. The residue is purified by "flash" chromatography [eluent: chloroform/methanol (97.5/2.5 by volume)]. Fractions 33 to 80 are combined and concentrated to dryness under reduced pressure (2.7 kPa) at 30° C. This gives 5δ-[3-(4-methylpiperazin-1-yl)prop-2-yl]thiomethylenepristinamycin $I_A$ (1.25 g) in the form of a beige powder melting at about 195° C.

NMR spectrum: 0.70 (dd; 1H: 5β₂), 1.25 (d; 3H:

2.30 (s; 3H: >N—CH₃), 2.50 (up; 10H:

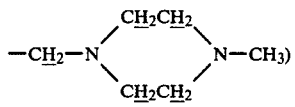

3.40 (dd; 1H: 5ε₂), 7.85 (dd broad; 1H: 1'H₆).

A 10% aqueous solution of 5δ-[3-(4-methylpiperazin-1-yl)prop-2-yl]thiomethylenepristinamycin I$_A$ (product AAN) in the form of the hydrochloride is obtained with:
product AAN ... 0.03 g
0.1N hydrochloric acid ... 0.3 cc The 1-(2-mercaptopropyl)-4-methylpiperazine is prepared by heating a mixture of propylene sulphide (19 cc) and N-methylpiperazine (29 cc) at 100° C. for 16 hours. This gives a colourless oil (32 g) distilling at 105° C. under 1.3 kPa.

APPLICATION EXAMPLE 35

By following a procedure analogous to that described in Application Example 34, but starting from 5δ-(4-methylphenyl)sulphonyloxymethylenepristinamycin I$_A$ (5.2 g), 1-dimethylaminopropane-2-thiol (0.6 g) and sodium ethylate (0.34 g), and after purification by "flash" chromatography [eluent: chloroform/methanol (95/5 by volume)] and concentration to dryness of fractions 16 to 38 under reduced pressure (2.7 kPa) at 30° C., 5δ-(3-dimethylaminoprop-2-yl)thiomethylenepristinamycin I$_A$ (1 g) is obtained in the form of a yellow powder melting at 172° C.

NMR spectrum: 0.65 (dd; 1H: 5β₂) 1.10 (d; 3H:

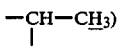

2.30 (s; 6H: —N(CH₃)₂) 7.60 (s broad; 1H: =CH—S—) 7.85 (dd; 1H: 1'H₆)

A 5% aqueous solution of 5δ-(3-dimethylaminoprop-2-yl)thiomethylenepristinamycin I$_A$ (product AAO) in the form of the hydrochloride is obtained with:
product AAO ... 0.03 g
0.1N hydrochloric acid ... 0.3 cc
distilled water ... q.s. 0.6 cc The 1-dimethylaminopropane-2-thiol can be prepared according to the method described by S. D. TURK et al., J. Org. Chem. 29, 974 (1964).

APPLICATION EXAMPLE 36

By following a procedure analogous to that described in Application Example 34, but starting from 5δ-(4-methylphenyl)sulphonyloxymethylenepristinamycin I$_A$ (6.3 g), 5-diethylaminopentane-2-thiol (1.05 g) and sodium ethylate (0.408 g), and after purification by "flash" chromatography [eluent: chloroform/methanol (97.5/2.5 by volume)] and concentration to dryness of fractions 47 to 65 under reduced pressure (2.7 kPa) at 30° C., 5δ-(5-diethylaminopent-2-yl)thiomethylenepristinamycin I$_A$ (1.32 g) is obtained in the form of a beige powder melting at about 185° C.

NMR spectrum: 0.65 (dd; 1H: 5β₂) 1.20 (t; 6H: —N(CH₂CH₃)₂) 1.40 (d; 3H:

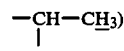

1.70 (s broad; 4H: —CH(CH₂)₂—CH₂N<) 2.65 (q; 4H: —N(CH₂—CH₃)₂) 3.50 (dd; 1H: 5ε₂) 7.65 (s broad; 1H: =CH—S—) 7.85 (dd; 1H: 1'H₆)

A 10% aqueous solution of 5δ-(5-diethylaminopent-2-yl)thiomethylenepristinamycin I$_A$ (product AAP) in the form of the hydrochloride is obtained with:
product AAP ... 0.05 g
0.1N hydrochloric acid ... 0.5 cc The 5-diethylaminopentane-2-thiol can be prepared in a manner analogous to that described in Application Example 22 for preparing 3-dimethylamino-2-methylpropanethiol, but starting from N,N-diethyl-4-acetylthiopentan-1-amine (4.0 g) and sodium (0.046 g). After purification by "flash" chromatography [eluent: ethyl acetate/methanol (70/30 by volume)] and concentration to dryness of fractions 16 to 24, 5-diethylaminopentane-2-thiol (2.0 g) is obtained in the form of a yellow oil.

The N,N-diethyl-4-acetylthiopentan-1-amine can be prepared in a manner analogous to that described in Application Example 22 for preparing N,N-dimethyl-3-acetylthio-2-methylpropylamine, but starting from N,N-diethyl-4-chloropentan-1-amine (32 g) and thiolacetic acid (15.2 g). This gives a product (4.31 g) in the form of a yellow oil.

The N,N-diethyl-4-chloropentan-1-amine can be prepared according to the method described by M. S. Kharash and C. F. Fuchs, U.S. Pat. No. 2,432,905.

APPLICATION EXAMPLE 37

A solution of 5δ-[(4-methylphenyl)sulphonyloxymethylene]pristinamycin I$_A$ (7.6 g) in tetrahydrofuran (60 cc) is cooled to a temperature of the order of −10° C. A solution of 2-dimethylaminoethanol (0.65 g) in tetrahydrofuran (60 cc), to which a 50% dispersion of sodium hydride in mineral oil (0.35 g) has been added, is added slowly to the first solution, the said temperature being maintained. When the addition has ended, the temperature is allowed to rise slowly to about 20° C. The reaction mixture is stirred for 24 hours at this temperature and then diluted with methylene chloride (500 cc) and washed with a saturated solution of ammonium chloride (2×50 cc). The organic phase is dried over magnesium sulphate and filtered and the filtrate is then concentrated to dryness under reduced pressure (2.7 kPa) at 40° C. The residue obtained is purified by "flash" chromatography [eluent: chloroform/methanol (95/5 by volume)]. Fractions 12 to 17 are combined and concentrated to dryness under reduced pressure (2.7 kPa) at 25° C. This gives 5δ-(2-dimethylaminoethoxymethylene)pristinamycin I$_A$ (1.5 g) in the form of a beige powder melting at about 160° C.

NMR spectrum: 0.65 (dd: 1H: 5β₂) 2.3 (s; 6H: —N(CH₃)₂) 2.65 (up; 2H: —CH₂N<) 3.42 (dd; 1H: 5ε₂) 4.15 (t; 2H: —OCH₂—) 5.15 (d; 1H: 5ε₁) 7.45 (under the aromatic protons; 1H: >C=CHO—) 7.80 (dd; 1H: 1'H₆)

A 1% aqueous solution of 5δ-(2-dimethylaminoethoxymethylene)pristinamycin I$_A$ (product AAQ) in the form of the hydrochloride is obtained with:
product AAQ ... 0.03 g 0.1N hydrochloric acid . . . 0.3 cc
distilled water . . . q.s. 3 cc

APPLICATION EXAMPLE 38

4-Amino-1-methylpiperidine (0.12 g) is added, at a temperature of the order of 20° C., to a solution of 5δ-(4-methylphenyl)sulphonyloxymethylenepristinamycin $I_A$ (0.5 g) in ethanol (25 cc). After stirring for 16 hours at this temperature, the reaction mixture is diluted with methylene chloride (100 cc) and washed twice with distilled water (100 cc in total). The organic phase is dried over sodium sulphate and then concentrated under reduced pressure (2.7 kPa) at 30° C. The residue is stirred with ethyl ether (15 cc). After filtration, 5δ-(1-methylpiperidin-4-yl)aminomethylenepristinamycin $I_A$ (0.42 g) is obtained in the form of a white powder, the characteristics of which are identical to those described in Application Example 14.

The 4-amino-1-methylpiperidine can be prepared as indicated in Application Example 14.

APPLICATION EXAMPLE 39

5δ-(1-Methylpiperidin-4-yl)aminomethylenepristinamycin $I_A$, described in Application Example 14 (designated below by "Amine of application 14"), and 5δ-(3-dimethylaminopropyl)thiomethylenepristinamycin $I_A$, described in Application Example 20 (designated below by "Thiol of application 20"), were prepared from the products of the general formula (I) described in Examples 3, 5, 6, 8, 10, 11, 12, 13, 14, 15, 21, 22 and 24. The operating conditions are indicated in the following table:

| Starting material (reference number of the example) | Reaction conditions (solvent, temperature, duration) | Product prepared |
|---|---|---|
| 3 | CH₃COOH, 20° C. 20 hours | Amine of application 14 |
| 5 | CH₃COOH/CF₃COOH, 20° C., 20 hours | Thiol of application 20 |
| 6 | CH₃COOH, 20° C. 20 hours | Amine of application 14 |
| 8 | CH₃COOH/CF₃COOH, 20° C., 48 hours | Amine of application 14 |
| 11 | CH₃COOH/CF₃COOH, 20° C., 20 hours | Thiol of application 20 |
| 12 | CH₃COOH/CF₃COOH, 20° C., 48 hours | Thiol of application 20 |
| 13 | CH₃COOH, 20° C. 20 hours | Thiol of application 20 |
| 14 | CH₃COOH, 20° C., 10 days | Amine of application 14 |
| 15 | CH₃COOH/CF₃COOH, 20° C., 20 hours | Thiol of application 20 |
| 21 | CH₃COOH, 20° C. 6 hours | Amine of application 14 |
| 22 | CH₃COOH, 20° C. 20 hours | Amine of application 14 |
| 24 | C₂H₅OH, 20° C. 20 hours | Thiol of application 20 |

In human therapy, the products of the general formula (IX) are particularly useful in the treatment of infections of bacterial origin.

The doses depend on the desired effect and the duration of the treatment; for an adult, they are generally between 2000 and 4000 mg per day, administered parenterally, in particular intravenously by slow perfusion.

In general, the physician will determine the dosage which he considers to be most appropriate as a function of the age, the weight and all the other factors peculiar to the subject to be treated.

We claim:

1. A synergistine of the formula:

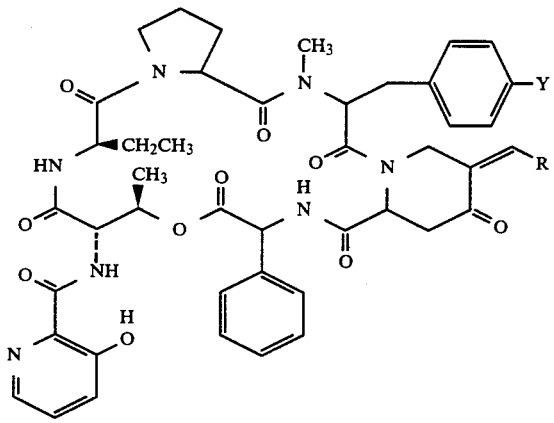

in which Y represents hydrogen or dimethylamino, and R represents:
  (a) hydrogen or hydroxyl;
  (b) a radical of the formula:

in which $R_1$ and $R_2$, which are identical or different, each represent
  (i) hydrogen;
  (ii) phenyl or pyridyl each of which is unsubstituted or substituted by a dialkylamino radical of which the alkyl part has 1 to 4 carbon atoms in a linear or branched chain,
  (iii) alkyl of 1 to 10 carbon atoms in a linear or branched chain, which is unsubstituted or substituted by hydroxyl, mercapto, carboxyl, pyridyl or anilino or substituted by alkylamino or dialkylamino of which at least one alkyl is itself substituted by hydroxyl, mercapto, carboxyl or anilino,
  (iv) alkenyl of 3 or 4 carbon atoms or
  (v) alkynyl of 3 to 4 carbon atoms, or alternatively
  (vi) $R_1$ and $R_2$ together form, with the nitrogen atom to which they are bonded, a 5-membered or 6-membered heterocyclic ring, which is unsubstituted or substituted by an alkyl radical, or
  (c) a halogen atom, a trimethylsilyloxy or dialkylphosphoryloxy radical or a radical of the formula:

—OSO₂R₃ or —OCOR₄ in which $R_3$ is alkyl, trifluoromethyl or trichloromethyl or phenyl unsubstituted or substituted by halogen or by alkyl or nitro, and $R_4$ is defined in the same way as $R_3$ or represents alkylcarbonylmethyl, 2-alkylcarbonylethyl, alkoxycarbonylmethyl, 2-alkoxycarbonylethyl or alkoxy, the abovementioned alkyl portions or radicals being linear or branched unless stated otherwise and containing 1 to 4 carbon atoms each, in its isomeric forms where such exist and mixtures thereof, and also its addition salts with acids, its metal salts and its addition salts with nitrogen bases, when they exist.

2. A synergistine according to claim 1 in which R is hydrogen, hydroxyl, or a radical of formula: —NR$_1$R$_2$ in which R$_1$ and R$_2$ each represent hydrogen, phenyl, dialkylaminophenyl, alkyl, alkyl substituted by hydroxyl, mercapto, carbonyl, pyridyl, anilino, hydroxyalkylamino, or di(hydroxylalkyl)amino, or alkynyl of 3 to 4 carbon atoms.

3. A synergistine according to claim 1 which is 5δ-dimethylaminomethylenepristinamycin I$_A$ and its acid addition salts.

4. A synergistine according to claim 1 which is 5δ-dimethylaminomethylenevirginiamycin S and its acid addition salts.

5. A synergistine according to claim 1 which is 5δ-methylenepristinamycin I$_A$ and its acid addition salts.

6. A synergistine according to claim 1 which is 5δ-hydroxymethylenepristinamycin I$_A$ and its acid addition salts.

7. A synergistine according to claim 1 which is 5δ-methylenevirginiamycin S and its acid addition salts.

* * * * *